United States Patent
Adiyoso

(10) Patent No.: US 11,779,225 B2
(45) Date of Patent: Oct. 10, 2023

(54) HEMODYNAMIC ANALYSIS OF VESSELS USING RECURRENT NEURAL NETWORK

(71) Applicant: Siemens Healthcare GmbH, Erlangen (DE)

(72) Inventor: Arnaud Arindra Adiyoso, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 457 days.

(21) Appl. No.: 16/891,192

(22) Filed: Jun. 3, 2020

(65) Prior Publication Data
US 2020/0390342 A1   Dec. 17, 2020

(30) Foreign Application Priority Data

Jun. 11, 2019  (EP) .................................... 19179348

(51) Int. Cl.
*A61B 5/02*         (2006.01)
*G16H 50/30*        (2018.01)
*A61B 5/029*        (2006.01)

(52) U.S. Cl.
CPC ...... *A61B 5/02028* (2013.01); *A61B 5/02007* (2013.01); *A61B 5/029* (2013.01); *G16H 50/30* (2018.01)

(58) Field of Classification Search
CPC . A61B 5/02028; A61B 5/02007; A61B 5/029; G16H 50/50; G16H 50/20; G06N 3/0454; G06N 3/0481; G06N 3/049; G06N 3/084; G06F 30/27; G06F 30/28
See application file for complete search history.

(56) References Cited

U.S. PATENT DOCUMENTS 6,377,832 B1 *  4/2002  Bergman ............. A61B 5/7264
                                                        600/408
10,249,048 B1 * 4/2019  Wang ................ A61B 5/02028
                        (Continued)

FOREIGN PATENT DOCUMENTS

CN        106980899 A  *  7/2017  ................ G06N 3/08
CN        108992057 A  * 12/2018  ........... A61B 5/0263
                        (Continued)

OTHER PUBLICATIONS

CN-106980899-A (Year: 2017).*
(Continued)

*Primary Examiner* — Joel Lamprecht
*Assistant Examiner* — Nyrobi Celestine
(74) *Attorney, Agent, or Firm* — Harness, Dickey & Pierce, P.L.C.

(57) ABSTRACT

A method of and an Artificial Intelligence (AI) system for predicting hemodynamic parameters for a target vessel, in particular of an aorta, as well as to a computer-implemented method of training an AI unit of the AI system are disclosed. A vessel shape model of the target vessel and a corresponding flow profile of the target vessel are received. At least one hemodynamic parameter is predicted by the AI unit based on the received vessel shape model and the received flow profile. The AI unit is arranged and configured to predict at least one hemodynamic parameter based on a received vessel shape model and a received flow profile of the target vessel (aorta).

21 Claims, 9 Drawing Sheets

(56) References Cited

U.S. PATENT DOCUMENTS

| | | | |
|---|---|---|---|
| 2010/0128940 A1* | 5/2010 | Buelow | G06T 7/149 |
| | | | 382/128 |
| 2011/0081057 A1* | 4/2011 | Zeng | G06T 7/0012 |
| | | | 382/128 |
| 2015/0112182 A1 | 4/2015 | Sharma et al. | |
| 2018/0078139 A1* | 3/2018 | Sanders | G16H 50/70 |
| 2018/0366224 A1 | 12/2018 | Neumann | |
| 2019/0000554 A1* | 1/2019 | Taylor | A61B 5/1118 |
| 2019/0159737 A1* | 5/2019 | Buckler | G06T 7/0012 |
| 2019/0188510 A1* | 6/2019 | Han | G06V 40/172 |
| 2019/0362855 A1* | 11/2019 | Ma | A61B 6/5217 |
| 2020/0160509 A1* | 5/2020 | Pack | G16H 30/40 |

FOREIGN PATENT DOCUMENTS

| | | |
|---|---|---|
| EP | 3270308 A1 | 1/2018 |
| WO | WO 2016075331 A2 | 5/2016 |
| WO | WO 2019025270 A1 | 2/2019 |

OTHER PUBLICATIONS

R. Bates et al., "Extracting 3D Vascular Structures from Microscopy Images using Convolutional Recurrent Networks," arXiv, pp. 1-8, May 2017 (Year: 2017).*

D. Zhang et al., "Cascade and Parallel Convolutional Recurrent Neural Networks on EEG-based Intention Recognition for Brain Computer Interface," Thirty-Second AAAI Conference on Artificial Intelligence, Nov. 2017 (Year: 2017).*

CN-108992057-A (Year: 2018).*

J. Fan et al., "A Selective Overview of Deep Learning", pp. 1-37, Apr. 2019 (Year: 2019).*

Y. Wang et al., "Generalized Recurrent Neural Network accommodating Dynamic Causal Modelling for functional MRI analysis," Neuroimage, vol. 178, pp. 1-59, Sep. 2018 (Year: 2018).*

Ladisa, John F. et al. "Aortic coarctation: Recent developments in experimental and computational methods to assess treatments for this simple condition", Progress in Pediatric Cardiology, 2010, vol. 30, pp. 45-49.

Nørgaard, Bjarne L., et al. "Diagnostic performance of noninvasive fractional flow reserve derived from coronary computed tomography angiography in suspected coronary artery disease: the NXT trial (Analysis of Coronary Blood Flow Using CT Angiography: Next Steps)." Journal of the American College of Cardiology 63.12 (2014): 1145-1155.; 2014.

Hellmeier et al "Hemodynamic Evaluation of a Biological and Mechanical Aortic Valve Prosthesis Using Patient-Specific MRI-Based CFD"; Artif Organs, Jan. 2018; 42(1): 49-57. doi: 10.1111/aor.12955. Epub Aug. 29, 2017.

Kelm, M. et al. "Model-Based Therapy Planning Allows Prediction of Haemodynamic Outcome after Aortic Valve Replacement", Scientific Reports, 2016, https://doi.org/10.1038/s41598-017-03693-x.

Qi, C. et. al., "PointNet: Deep Learning on Point Sets for 3D Classification and Segmentation", arXiv:1612.00593, 2017.

Kissas, Georgios et al: "Machine learning in cardiovascular flows modeling: Predicting arterial blood pressure from non-invasive 4D flow MRI data using physics-informed neural networks"; Computer Methods in Applied Mechanics and Engineering; North-Holland, Amsterdam, NL; vol. 358; Sep. 17, 2019; XP085907007; ISSN: 0045-7825; DOI: 10.1016/J.CMA.2019.112623; 2019.

Sun, Luning et al: "Surroqate Modeling for Fluid Flows Based on Physics-Constrained Deep Learning Without Simulation Data"; arxiv.org; Cornell University Library, 201 Olin Library Cornell University Ithaca, NY 14853; Jun. 6, 2019; XP081373782; pp. 1-34; URL: https://arxiv.org/abs/1906.02382 [retrieved on Dec. 12, 2019]; 2019.

European Search Report for European Patent Application No. 19179348 dated Dec. 16, 2019.

* cited by examiner

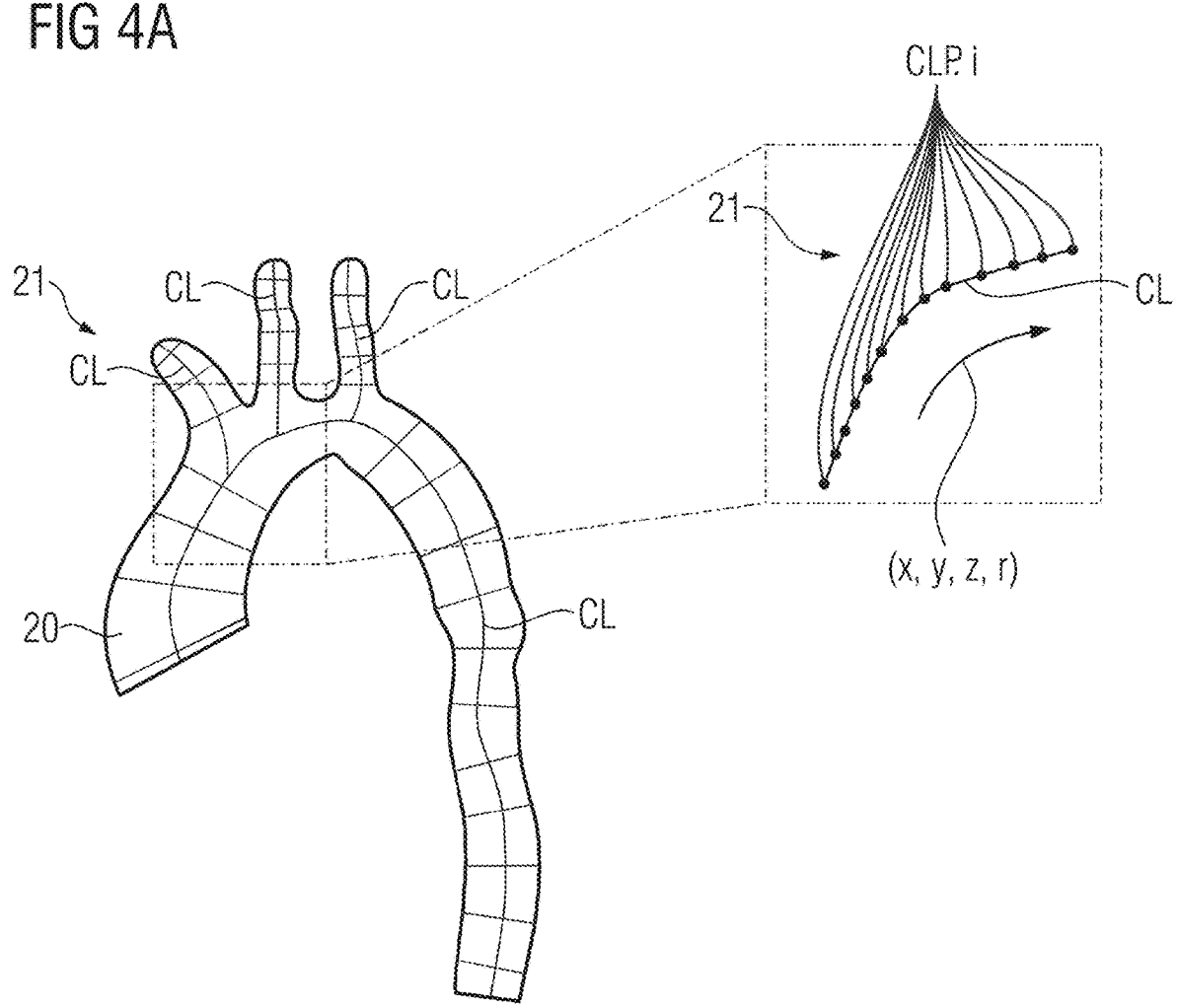

HEMODYNAMIC ANALYSIS OF VESSELS USING RECURRENT NEURAL NETWORK

PRIORITY STATEMENT

The present application hereby claims priority under 35 U.S.C. § 119 to European patent application number EP 19179348.8 filed Jun. 11, 2019, the entire contents of which are hereby incorporated herein by reference.

FIELD

Embodiments of the present invention are generally related to a method of and an Artificial Intelligence (AI) system for predicting hemodynamic parameters for a target vessel as well as to a computer-implemented method of training an AI unit comprised by the AI system.

BACKGROUND

Coarctation of the aorta and aortic valve disease are the most common congenital heart defects. Treatment decision making for these diseases is a complex process and is highly dependent on the condition of the patients. Based on patient-specific hemodynamic parameters of the patient's aorta the treatment decision can be significantly improved. The current clinical standard in assessing hemodynamic parameters is to perform the catheterization technique. However, the catheterization technique is an invasive procedure that poses risks for patients (e.g., radiation, cost, complications).

Non-invasive methods using different computational fluid dynamics (CFD) approaches are being extensively validated. These methods are increasingly considered to replace the invasive methods, as they have less risk and could provide more holistic and relevant information. However, these CFD approaches are computationally expensive, which is a limiting factor in the implementation of such tool in the clinic.

To improve the treatment decision making, hemodynamic analysis using Computational Fluid Dynamic (CFD) simulations could be performed. CFD simulations compute patient-specific hemodynamic parameters that could be used to better assess the condition of the patients and optimise the clinical decision. However, CFD simulations are highly computationally demanding and require up to one day per scan to be completed. This prohibits the integration of hemodynamic analysis based on CFD simulations in clinical practice.

Consequently, there is a need to provide an alternative approach or method that computes the hemodynamic parameters more efficiently without the need for complex CFD simulations.

EP 3 270 308 A1 discloses a method for providing a secondary parameter like a hemodynamic parameter inside a vessel to a Clinical Decision Support (CDS) system. A shape dataset of the vessel is extracted from an image dataset and provided as input dataset. The secondary parameter is approximated based on the input dataset using a sub-system trained by machine learning (deep learning mechanism).

SUMMARY

The inventors have discovered that the approximated secondary parameter or rather hemodynamic parameter inside the vessel has to be exactly determined, otherwise this may lead to misdiagnosis by a CDS system or a clinician based on the approximated hemodynamic parameter.

Further, the inventors have discovered that no appropriate machine learning approach has been proposed for this task at hand. This is likely because big data is to be used to develop the algorithm, which big data is, however, not readily available.

At least one embodiment of the present invention is directed to overcoming or at least alleviating at least one of these problems by providing a method of predicting hemodynamic parameters for a target vessel of an embodiment; and/or an AI system of an embodiment for predicting hemodynamic parameters for a target vessel; and/or a computer-implemented method of training an AI unit of an embodiment comprised by the AI system of an embodiment. Further refinements of the present invention are subject of the claims.

According to a first embodiment of the present invention, a method of predicting hemodynamic parameters $p_k$ for a target vessel comprises:
  receiving a vessel shape model of the target vessel;
  receiving a corresponding flow profile of the target vessel; and
  predicting at least one hemodynamic parameter $p_k$ based on the received vessel shape model and the received flow profile by an Artificial Intelligence (AI) unit.

According to a second embodiment of the present invention, an AI system for predicting hemodynamic parameters ($p_k$) for a target vessel is arranged and configured to, in at least one embodiment, execute the method according to the first embodiment of the present invention. The AI system of an embodiment comprises a first interface, a second interface and an AI unit. The first interface is arranged and configured to receive a vessel shape model of the target vessel. The second interface is arranged and configured to receive a corresponding flow profile of the target vessel. The AI unit is communicatively connected to the first interface and to the second interface. The AI unit is arranged and configured to predict at least one hemodynamic parameter ($p_k$) based on the received vessel shape model and the received flow profile.

According to a third embodiment of the present invention a computer program comprises instructions which, when the program is executed by a computer, cause the computer to carry out the steps of the method according to the first embodiment of the present invention.

According to a fourth embodiment of the present invention a computer-readable medium has stored thereon the computer program according to the third embodiment of the present invention.

According to a fifth embodiment of the present invention a data processing system comprises structure for carrying out the steps of the method according to the first embodiment of the present invention.

According to a sixth embodiment of the present invention a computer-implemented method of training an Artificial Intelligence (AI) unit, preferably a Recurrent Neural Network (RNN) and most preferably a Long Short Term Memory (LSTM) network, as comprised by the AI system according to the second embodiment of the present invention comprises:
  receiving an input training dataset comprising training vessel shape models and corresponding training flow profiles;
  receiving an output training dataset corresponding to the received training input dataset comprising corresponding training hemodynamic parameters; and
  training the AI unit to predict at least one hemodynamic parameter $p_k$ of a target vessel with the received training vessel shape models and corresponding training flow profiles and the received set of corresponding training outputs.

According to a seventh embodiment of the present invention a computer program comprises instructions which, when the program is executed by a computer, cause the computer to carry out the steps of the method according to the embodiment aspect of the present invention.

According to an eighth embodiment of the present invention a computer-readable medium has stored thereon the computer program according to the seventh embodiment of the present invention.

According to a ninth embodiment of the present invention a data processing system comprises a device/apparatus for carrying out the steps of the method according to the sixth embodiment of the present invention.

BRIEF DESCRIPTION OF THE DRAWINGS

Embodiments of the present invention and its technical field are subsequently explained in further detail by example embodiments shown in the drawings. The example embodiments only conduce better understanding of the present invention and in no case are to be construed as limiting for the scope of the present invention. Particularly, it is possible to extract aspects of the subject-matter described in the figures and to combine it with other components and findings of the present description or figures, if not explicitly described differently. Equal reference signs refer to the same objects, such that explanations from other figures may be supplementally used.

FIG. 4A shows a schematic view of an example vessel shape model of an aorta of a human subject.

DETAILED DESCRIPTION OF THE EXAMPLE EMBODIMENTS

Figure 1:
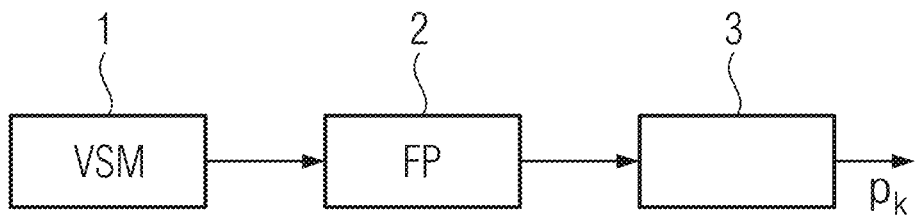
FIG. 1 shows a schematic flow chart of an embodiment of the method of predicting hemodynamic parameters according to the first aspect of the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central At least one processor (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central At least one processor (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer at least one processors into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to a first embodiment of the present invention, a method of predicting hemodynamic parameters $p_k$ for a target vessel comprises:

receiving a vessel shape model of the target vessel;

receiving a corresponding flow profile of the target vessel; and predicting at least one hemodynamic parameter pk based on the received vessel shape model and the received flow profile by an Artificial Intelligence (AI) unit.

According to a second embodiment of the present invention, an AI system for predicting hemodynamic parameters ($p_k$) for a target vessel is arranged and configured to, in at least one embodiment, execute the method according to the first embodiment of the present invention. The AI system of an embodiment comprises a first interface, a second interface and an AI unit. The first interface is arranged and configured to receive a vessel shape model of the target vessel. The second interface is arranged and configured to receive a corresponding flow profile of the target vessel. The AI unit is communicatively connected to the first interface and to the second interface. The AI unit is arranged and configured to predict at least one hemodynamic parameter ($p_k$) based on the received vessel shape model and the received flow profile.

According to a third embodiment of the present invention a computer program comprises instructions which, when the program is executed by a computer, cause the computer to carry out the steps of the method according to the first embodiment of the present invention.

According to a fourth embodiment of the present invention a computer-readable medium has stored thereon the computer program according to the third embodiment of the present invention.

According to a fifth embodiment of the present invention a data processing system comprises structure for carrying out the steps of the method according to the first embodiment of the present invention.

At least one embodiment of the present invention provides a novel method and algorithm, respectively, for hemodynamic parameter prediction using an AI unit and, in particular, using a Recurrent Neural Network (RNN) like a Long Short Term Memory (LSTM) network.

The at least one hemodynamic parameter $p_k$ of the target vessel may be at least one of a systolic blood pressure, a diastolic blood pressure, an arterial blood pressure, a mean arterial pressure, a systolic pressure variation, a pulse pressure variation, a stroke volume variation, a right atrial pressure, a right ventricular pressure, a pulmonary artery pressure, a mean pulmonary artery pressure, a pulmonary artery wedge pressure, a left arterial pressure, a cardiac output, a cardiac index, a stroke volume, a systemic vascular resistance, a systemic vascular resistance index, a pulmonary vascular resistance, a pulmonary vascular resistance index, a left ventricular stroke work, a left ventricular stroke work index, a right ventricular stroke work, a right ventricular stroke work index, a coronary artery perfusion pressure, a right ventricular end-diastolic volume, a right ventricular end-systolic volume, a right ventricular ejection fraction or the like.

The target vessel may be any vessel of a human or animal body that is subject of a diagnosis or planned intervention or a part or section of such vessel. In particular, the target vessel may be an aorta or rather a part of the aorta of a patient.

The vessel shape model of the target vessel is the first input that is used to predict the at least one hemodynamic parameter of the target vessel. The vessel shape model of the target vessel may be a dataset representing any kind of polygonal mesh. For example, the dataset comprises a set of vertices, triangles and/or polygons that form two-dimensional (2D) or three-dimensional (3D) meshes. The vessel shape model or dataset can also comprise volumetric meshes formed from vertices, tetrahedra, hexahedra or other 3D elements. Preferably, the vessel shape model comprises a segmentation of a surface of a 3D vessel, in particular an aorta, wherein the surface is derived from an image dataset. For example, the vessel shape model is extracted from an image dataset showing an aorta of a patient. Further, the vessel shape model may comprise a centreline extending from an inlet to an outlet of the target vessel, where the centreline runs through all centre points along the target vessel, and the corresponding diameters of the target vessel.

The corresponding flow profile of the target vessel is the second input that is used to predict the at least one hemodynamic parameter of the target vessel. The corresponding flow profile of the target vessel comprises features of the blood flow in the target vessel. Preferably, the flow profile comprises at least three and up to 100 features. Most preferably, the flow profile comprises 16 features. For example, the flow profile may comprise blood flow velocities, derived features which are computed based on the blood flow velocities like secondary flow degrees etc., boundary conditions like input flow rate, output flow rate etc. The flow profile may comprise the features only for an inlet of the target vessel or rather for a vessel shape point at an inlet of the vessel shape model of the target vessel.

The at least one hemodynamic parameter is predicted based on the information and features contained in the vessel shape model and the corresponding flow profile of the target vessel (at the inlet). In particular, the at least one hemodynamic parameter may be predicted at the at least one vessel shape point of the vessel shape model based on the three coordinates x, y, z of the at least one vessel shape point and the respective radius r of the target vessel as well as on the features of the flow profile (e.g. blood flow velocities) at the inlet of the target vessel.

The vessel shape model of the target vessel is provided via the first interface of the AI system. The corresponding flow profile of the target vessel is provided via the second interface of the AI system. The first input and second input are forwarded to the AI unit of the AI system. The at least one hemodynamic parameter is predicted by the AI unit. The AI unit, which may be an Artificial Neural Network (ANN), is trained for predicting the hemodynamic parameter based on the vessel shape model and the corresponding flow profile (at the inlet) of the target vessel.

Artificial neural networks (ANN) are systems, in particular computing systems, inspired by biological neural networks that constitute animal brains. ANNs "learn" to perform tasks by considering (labelled) examples or training data, generally without being designed with any task-specific rules. During an initial learning or training phase ANNs automatically generate identifying characteristics from the (labelled) training data. ANNs comprise a collection of connected nodes called artificial neurons, which loosely model the neurons in a biological brain. Each connection (synapses in the biological brain) can transmit a signal from one node to another. A node that receives a signal can process it and then signal to subsequent neurons connected to it. In common ANN implementations, the signal at a connection between nodes is a real number (e.g. 0 . . . 1), and the output of each artificial neuron is computed by some non-linear function of the sum of its inputs (from other nodes). The connections between nodes are called "edges". The edges in ANNs may each have a weight that is adjusted during training of the ANNs. The weight increases or decreases the strength of the signal at the corresponding edge. Nodes may each have a threshold such that the signal is only sent if an aggregate signal exceeds that threshold. Typically, nodes are aggregated into layers. Different layers may perform different kinds of transformations on their inputs. Signals travel from a first layer or input layer to a last layer or output layer, possibly after traversing the layers multiple times.

In other words, an ANN is a network of simple elements, the so-called nodes or artificial neurons, which receive input. After receiving input, the nodes change their internal state (activation) according to that input, and produce output depending on the input and activation. The network forms by connecting the output of certain nodes to the input of other nodes forming a directed, weighted graph. The weights as well as the functions that compute the activation of each node can be modified during initial learning/training, which is governed by a learning rule or paradigm.

A node receiving an input from at least one predecessor neuron consists of the following components: an activation, the node's state, depending on a discrete time parameter, optionally a threshold, which stays fixed unless changed by a learning/training function, an activation function (e.g. hyperbolic tangent function, sigmoid function, softmax function, rectifier function etc.) that computes the new activation at a given time and the net input and an output function computing the output from the activation (often the output function is the identity function). An important characteristic of the activation function is that it provides a smooth transition as input values change, i.e. a small change in input produces a small change in output.

An input node has no predecessor but serves as input interface for the whole ANN. Similarly, an output node has no successor and thus serves as output interface of the whole ANN. An ANN consists of edges/connections, each edge transferring the output of a node (predecessor) to the input of another, succeeding node (successor). Additionally to the assigned weight an edge may have a bias term added to a total weighted sum of inputs to serve as a threshold to shift the activation function. The propagation function computes the input to the succeeding node (successor) from the outputs of preceding nodes (predecessors) and may include the bias value.

Based on the forwarded vessel shape model and flow profile (at the inlet) of the target vessel as inputs the AI unit predicts the at least one hemodynamic parameter (at the at least one vessel shape point).

The proposed method or rather algorithm can be executed substantially faster compared to existing methods using Computational Fluid Dynamics (CFD) or common AI methods. In particular the additional information contained in the (inlet) flow profile, which is provided as additional input besides the vessel shape model to the above described AI unit, facilitates more precise (in particular compared to common AI methods) and faster (in particular compared to methods using CFD) or even real-time prediction of the at least one hemodynamic parameter. The predicted at least one hemodynamic parameter could assist clinicians in performing complex treatment assessment for patients with, for example, coarctation of the aorta.

According to a refinement of at least one embodiment of the present invention the at least one hemodynamic parameter is predicted for at least one vessel shape point of the received vessel shape model in the step of predicting.

The vessel shape model comprises at least one vessel shape point having a first coordinate in a first direction x, a second coordinate in a second direction y perpendicular to the first direction x and a third coordinate in a third direction z perpendicular to the first direction x and the second direction y. The at least one vessel shape point of the vessel shape model may lay on the centreline of the target vessel or rather vessel shape model of the target vessel and may comprise a radius r of the target vessel at the respective position of the vessel shape point along the centreline. Additionally, the at least one vessel shape point may contain further information like change of radius of the target vessel, position along the centreline, and the like.

Instead of predicting the at least one hemodynamic parameter at each point of the target vessel, the prediction is made only for the provided vessel shape points of the vessel shape model of the target vessel. For example, the vessel shape model may comprise a multitude of vessel shape points (e.g. 100 to 500) along the centreline, where each vessel shape point comprises its coordinates x, y, z and the radius r of the target vessel at the respective vessel shape point. The at least one hemodynamic parameter may be predicted by the AI unit at each given vessel shape point of the vessel shape model.

By predicting the at least one hemodynamic parameter only at the given vessel shape points of the vessel shape model instead of at every node of a mesh of the vessel shape model, the computational effort can be significantly reduced. Yet, the informative value is high, such that a clinical decision can be made (by a clinician or a CDS system) based on the provided at least one hemodynamic parameter at the given vessel shape points.

According to a refinement of at least one embodiment of the present invention the step of predicting is iteratively executed for each of at least two consecutive vessel shape points of the received vessel shape model.

At a first vessel shape point of the vessel shape model the at least one hemodynamic parameter is predicted by the AI unit based on the information comprised by the first vessel shape point as first input and based on the flow profile (at the inlet of the target vessel) as second input. At each succeeding vessel shape point succeeding the first vessel shape point, or in other words the next vessel shape points downstream the centreline, the second input to the AI unit is internal information, in particular, hidden state(s) of layer(s), of the AI unit from the preceding vessel shape point instead of the (inlet) flow profile. Consequently, each of the vessel shape points is iteratively stepped from the first vessel shape point to a last vessel shape point (along the centreline). For each vessel shape point the at least one hemodynamic parameter is predicted by the AI unit, where for the first vessel shape point the (inlet) flow profile and for any succeeding vessel shape point the internal information of the AI unit at the preceding vessel shape point is used as second input.

In Particular, the AI unit may comprise a Recurrent Neural Network, where the internal information of the RNN, namely the hidden states of the layers of the RNN, is remembered and used in succeeding iterations.

Due to the iterative execution of the step of predicting, where only for the first vessel shape point a flow profile is needed as second input to the AI unit, the amount of input data that has to be provided to the AI unit for predicting the at least one hemodynamic parameter at different vessel shape points can be significantly reduced.

According to a refinement of at least one embodiment of the present invention the AI unit comprises a Recurrent Neural Network, RNN, and preferably a Long Short Term Memory, LSTM, network.

RNNs are networks with loops in them, allowing information to persist. One layer of nodes of an RNN receives at some input and outputs a value or rather hidden state, while the respective loop allows information to be passed from one step to the next. LSTM networks are a special kind of RNN, capable of learning long-term dependencies by means of memory cells. All RNNS and LSTM networks have the form of a chain of repeating modules of neural network. In standard RNNs, this repeating module or rather layer of nodes has a simple structure (e.g. single tank layer). The repeating module in a standard RNN contains a single layer. LSTM networks also have a chain-like structure, but the repeating module has a different structure. Instead of having a single neural network layer, there are commonly four interacting layers in LSTM networks enabling a cell state for each repeating module/layer of nodes to be remembered by a memory cell. An LSTM network has the ability to remove or add information to the cell state in the memory cell via gates of the memory cell. Gates are commonly composed out of a sigmoid layer and a point-wise multiplication operation. The sigmoid layer outputs numbers between zero and one for weighting the output. An LSTM network commonly has three of these gates to protect and control the cell state in the memory cell.

An RNN and in particular a LSTM network increases efficiency, as only one (inlet) flow profile has to be provided for the first vessel shape point of the iteration, while for the following vessel shape points the respective remembered hidden states of the previous iteration can be used for predicting the at least one hemodynamic parameter.

According to a refinement of at least one embodiment of the present invention the step of predicting comprises the following iterative steps:

Providing to a first input block of the AI unit one vessel shape point of the received vessel shape model at each iteration i.

Providing to a second input block of the AI unit the received flow profile at a first iteration i=1.

Generating at least one current hidden state $h_{j,i}$, in a deduction block of the AI unit based on the provided one vessel shape point and on the provided flow profile at the first iteration i=1 or at least one previous hidden state of $h_{j,i-1}$ of the deduction block at any iteration i>1 subsequent to the first iteration.

Determining the at least one hemodynamic parameter $p_k$ in an output block of the AI unit based at least on a last generated current hidden state $h_{M,i}$ of the at least one generated current hidden states $h_{j,i}$.

According to a further refinement of at least one embodiment of the present invention the AI unit comprises a first input block, a second input block, a deduction block and an output block. The first input block is communicatively connected to the first interface and arranged and configured to get provided one vessel shape point of the received vessel shape model at each iteration i. The second input block is communicatively connected to the second interface and arranged and configured to get provided the received flow profile at a first iteration i=1. The deduction block is communicatively connected to the first input block and to the second input block. The deduction block is arranged and configured to generate at least one current hidden state $h_{j,i}$ based on the provided one vessel shape point and on the provided flow profile at the first iteration i=1 or at least one previous hidden state $h_{j,i-1}$ of the deduction block at any iteration i>1 subsequent to the first iteration. The output block is communicatively connected to the deduction block and arranged and configured to determine the at least one hemodynamic parameter $p_k$ based at least on a last generated current hidden state $h_{M,i}$ of the at least one generated current hidden states $h_{j,i}$.

For every vessel shape point (1 ... N) of the provided vessel shape model of the target vessel the at least one hemodynamic parameter $p_k$ is predicted in one iteration i, where i=1 ... N.

The first input block of the AI unit may comprise at least one layer. The layer(s) of the first input block may be fully connected and preferably comprise four to 512 nodes, most preferably 64 nodes. The second input block of the AI unit may comprise at least one layer. The layer(s) of the second input block may be fully connected and preferably comprise four to 512 nodes, most preferably 64 nodes. The deduction block of the AI unit may comprise at least one deduction layer (M is the number of layers of the deduction block, M≥1). The deduction layer(s) of the deduction block may be fully connected and preferably comprise four to 512 nodes, most preferably 64 nodes. The output block of the AI unit may comprise at least one layer and preferably at least one concatenation layer and one output layer. The layers of the output block may be fully connected and comprise preferably four to 512 (output) nodes, more preferably 64 (output) nodes. Most preferably the at least one concatenation layer comprises 48 nodes and the output layer comprises as many output nodes as there are hemodynamic parameters to be predicted by the AI unit.

For each vessel shape point of the provided vessel shape model of the target vessel one iteration i has to be executed to predict each respective at least one hemodynamic parameter.

At the first input block one vessel shape point is provided to the AI unit. The complete vessel shape model, received at the first interface, is stepped point-wise, such that at each iteration i one vessel shape point is provided to the first input block. Starting, at the first iteration i=1, with the first vessel shape point located closest to the inlet of the target vessel the vessel shape model is stepped until, at the last iteration i=N, the last vessel shape point located closest to an outlet of the target vessel is provided to the first input block.

At the first iteration i=1 where the first vessel shape point (at the inlet off the target vessel) is provided to the first input block, the flow profile received at the second interface is provided to the AI unit via the second input block. The flow profile preferably comprises information about or features of the blood flow at the inlet of the target vessel.

The information contained in the vessel shape point provided to the first input block and the information contained in the (inlet) flow profile provided to the second input block are transformed by the respective input blocks into features and provided to the deduction block. The deduction block uses the features (transformed input information) from the first and second input block to deduce at least one hidden state $h_{j,i}$. Based on the last hidden state $h_{M,i}$ of the deduction block the at least one hemodynamic parameter at the provided vessel shape point is predicted. Thereto, the last hidden state $h_{M,i}$ is provided to the output block which uses the last hidden state $h_{M,i}$ to determine the respective at least one hemodynamic parameter at the provided vessel shape point.

In any iteration i>1 subsequent to the first iteration there is no flow profile provided to the second input block. Instead of the flow profile as second input a hidden state hj, i−1 of the deduction block at the preceding iteration i−1 is provided as input to the deduction block in addition to the one vessel shape point.

The deduction block generates the at least one hidden state $h_{j,i}$ at each iteration i, where the last of the at least one hidden state $h_{M,i}$ (M is the number of layers of the deduction block, M≥1) contains all the information of the at least one hemodynamic parameter to be predicted, which information then is concatenated and combined in the output block into the at least one hemodynamic parameter.

For example, a vessel shape model of the target vessel (e.g. aorta) comprising three vessel shape points (along the centreline) may be provided to and received at the first interface. Further, an inlet flow profile with features of the blood flow at an inlet of the target vessel may be provided to and received at the second interface. The first vessel shape point may be located at the inlet of the target vessel. In order to predict at least one hemodynamic parameter at each of the vessel shape points, there have to be executed three iterations, one for each vessel shape point. In the first iteration i=1 the first vessel shape point is provided to the first input block as first input for the AI unit and the inlet flow profile is provided to the second input block as second input for the AI unit. The two input blocks transform the information contained in the first vessel shape point and the inlet flow profile, respectively, into features for the deduction block. The deduction block deduces at least one hidden state h1,1 based on the features provided by the first and second input block. Finally, the output block determines the at least one hemodynamic parameter at the first vessel shape point from the (last) hidden state h1,1 provided by the deduction block. In the next iterations i=2 and i=3 the second vessel shape point and then the last vessel shape point are provided to the first input block. The second input block is not provided with any input. The deduction block deduces the at least one hidden state h1,2 at the second iteration i=2 and the at least one hidden state h1,3 at the last iteration based on the features or rather transformed information of the second and last vessel shape point, respectively, provided by the first input block and based on the at least one hidden state h1,1 and h1,2, respectively, of the respective preceding iteration. The output block determines the at least one hemodynamic parameter at the second vessel shape point and at the last vessel shape point, respectively, based on the (last) hidden state h2,1 and h3,1, respectively, provided by the deduction block.

The two input blocks providing features to the deduction block based on the input data and the output block determining the at least one hemodynamic parameter from the last hidden state of the deduction block in each iteration, i.e. for each vessel shape point, facilitate particularly efficient prediction of hemodynamic parameters of the target vessel.

According to a refinement of at least one embodiment of the present invention the step of generating comprises the following steps:

Generating a first current hidden state $h_{1,i}$ in a first deduction layer of the AI unit based on the provided one vessel shape point and on the provided flow profile at the first iteration i=1 or a provided first previous hidden state $h_{1,i-1}$ of the first deduction layer at any iteration i>1 subsequent to the first iteration.

Optionally generating at least one further current hidden state $h_{j,i}$ in at least one further deduction layer of the AI unit based on the current hidden $h_{j-,i}$ state of the previous deduction layer and on an initial state $s_{j,1}$ of the at least one further deduction layer at the first iteration i=1 or a provided further previous hidden state $h_{j,i-1}$ of the at least one further deduction layer at any iteration i>1 subsequent to the first iteration.

Generating the last current hidden state $h_{M,i}$ in a last deduction layer of the AI unit based on the current hidden state $h_{M-1,i}$ of the previous deduction layer and on either an initial state $s_{M,1}$ of the last deduction layer or a provided last previous hidden state $h_{M,i-1}$ of the last deduction layer.

According to a further refinement of at least one embodiment of the present invention the AI unit comprises a first deduction layer, optionally at least one further deduction layer and a last deduction layer. The first deduction layer is communicatively connected to the first input block and to the second input block. The first deduction layer is arranged and configured to generate a first current hidden state $h_{1,i}$ based on the provided one vessel shape point and on the provided flow profile at the first iteration i=1 or a provided first previous hidden state of the first deduction layer at any iteration subsequent to the first iteration i>1. The optional at least one further deduction layer is communicatively connected to the first deduction layer. The optional at least one further deduction layer is arranged and configured to generate at least one further current hidden state based on the current hidden state $h_{j-1,i}$ of the previous deduction layer and on an initial state $s_{j,1}$ of the at least one further deduction layer at the first iteration i=1 or a provided further previous hidden state $h_{j,i-1}$ of the at least one further deduction layer at any iteration i>1 subsequent to the first iteration. The last deduction layer is communicatively connected to either the first deduction layer or the last of the at least one further deduction layer and arranged and configured to generate the last current hidden state $h_{M,i}$ based on the current hidden state $h_{M-1,i}$ of the previous deduction layer and on either an initial state $s_{M,1}$ of the last deduction layer at the first iteration i=1 or a provided last previous hidden state $h_{M,i-1}$ of the last deduction layer at any iteration i>1 subsequent to the first iteration.

The deduction block at least comprises one first deduction layer and one last deduction layer. Between the first and last deduction layer the deduction block may comprise further deduction layers. Preferably, the deduction block comprises in total 3 to 10 deduction layers (1 first layer, 1 to 8 further deduction layers and 1 last deduction layer, M=3 . . . 10).

The first of the at least one further deduction layer is communicatively connected to the first deduction layer and the last deduction layer is communicatively connected to the last of the at least one further deduction layer. Each of the at least one further deduction layer is consecutively communicatively connected with its adjacent deduction layers.

Based on the current vessel shape point as first input, the first input block provides information to the deduction block. Additionally, the second input block provides information based on the (inlet) flow profile to the deduction block at the first iteration i=1 or rather at the first vessel shape point of the provided vessel shape model of the target vessel. In the deduction block, the provided information is transformed into at least one first hidden state $h_{1,i}$ for the current iteration i by the first deduction layer. A first memory cell of the first deduction layer remembers the first current hidden state $h_{1,i}$ of the first deduction layer. This first current hidden state $h_{1,i}$ i is used in the subsequent iteration i+1. There may be further deduction layers consecutively communicatively connected to the first deduction layer using the first current hidden state $h_{1,i}$ for deducing further current hidden states $h_{j,i}$. The last deduction layer uses the first current hidden state $h_{1,i}$, if there are no further deduction layers between the first deduction layer and the last deduction layer of the deduction block (M=2), or rather the last of the further current hidden states $h_{M-1,i}$ provided by the last further deduction layer, if there are further deduction layers between the first deduction layer and the last deduction layer of the deduction block (M>2), to derive the last current hidden state $h_{M,i}$.

Each deduction layer has a memory cell having a predefined initial state $s_{j,1}$ at the beginning of the iteration. For each iteration 1>1 after the first iteration i=1 the second input block receives no flow profile as second input for the deduction block. Instead the deduction layers use, besides the current vessel shape point provided as first input via the first input block, the respective previous hidden state $h_{j,i-1}$ of itself at the previous iteration i−1 as additional input. The previous hidden state $h_{j,i-1}$ is remembered by the respective memory cell of the corresponding deduction layer and replaces the respective initial sate $s_{j,l}$ after the first iteration i=1. At the first iteration each memory cell of each deduction layer has the predetermined initial state $s_{j,1}$, which is used, except by the first deduction layer, in deriving the current hidden state $h_{j,i}$. These initial states $s_{j,1}$ of the memory cells of the deduction layers (except of the first deduction layer) can be seen as some sort of second input like the previous hidden state $h_{j,i-1}$ in the following iterations i>1.

Based on the last hidden state $h_{M,i}$ of each iteration i the output block determines the at least one hemodynamic parameter $p_k$ at the respective vessel shape point of the present iteration i.

A deduction block with a first and last deduction layer and optionally further deduction layers there between, provides for particularly precise and fast predictions of the at least one hemodynamic parameter.

According to a refinement of at least one embodiment of the present invention the vessel shape model comprises a centreline along a main direction of the target vessel. Further, each consecutive vessel shape point comprises a consecutive centreline point on the centreline and a radius of the target vessel at the respective centreline point.

The centreline runs through the centre of each section or slice of the target vessel. The radius r of the target vessel at each point along the centreline is orthogonal to the centreline. Each vessel shape point of the vessel shape model of the target vessel lays on the centreline. Each of the vessel shape points may comprise its coordinates (x, y, z) in 3D Cartesian coordinates or a distance along the centreline from the inlet. Further, each of the vessel shape points comprises the radius r of the target vessel at the respective vessel shape point.

The hemodynamic parameters at the points along the centreline give the most relevant information about the condition of the target vessel. Consequently, predicting the at least one hemodynamic parameter only at vessel shape points along the centreline provides for efficient determination of precise information regarding the condition of the target vessel that can be used by clinicians or a CDS system.

According to a refinement of at least one embodiment of the present invention the vessel shape model comprises a centreline along a main direction of the target vessel. Further, each consecutive vessel shape point comprises one consecutive centreline point on the centreline and a predetermined number k of surrounding points surrounding each centreline point in form of a sphere with the respective centreline point in the centre of the respective sphere. The step of generating comprises the following steps:

Generating first current hidden states $h_{1,i}$, $h_{1,i}^k$ in a first deduction layer of the AI unit based on the provided one vessel shape point including the respective centreline point and the k surrounding points surrounding the centreline point and on the provided flow profile at the first iteration i=1 or provided first previous hidden states $h_{1,i-1}$, $h_{1,i-1}^k$ of the first deduction layer at any iteration subsequent to the first iteration i>1.

Optionally generating at least one set of further current hidden states $h_{j,i}$, $h_{j,i}^k$ in at least one further deduction layer of the AI unit based on the current hidden states $h_{j-1,i}$, $h_{j-1,i}^k$ of the previous deduction layer and on initial states $s_{j,1}$, $s_{j,1}^k$ of the at least one further deduction layer at the first iteration i=1 or provided further previous hidden states $h_{j,i-1}$, $h_{j,i-1}^k$ of the at least one further deduction layer 13.j at any iteration subsequent to the first iteration i>1.

Generating the last current hidden states $h_{m,i}$m, $h_{M,i}^k$ in a last deduction layer of the AI unit based on the current hidden states $h_{M-1,i}$, $h_{M-1,i}^k$ of the previous deduction layer and on either initial states $s_{M,1}$, $s_{M,1}^k$ of the last deduction layer or provided last previous hidden states $h_{M,i-1}$, $h_{M,i-1}^k$ of the last deduction layer.

In the step of determining, the at least one hemodynamic parameter $p_k$ is determined in the output block of the AI unit based on the last generated current hidden states $h_{M,i}$, $h_{M,i}^k$.

According to a further refinement of at least one embodiment of the present invention the first input block is arranged and configured to get provided one vessel shape point comprising one consecutive centreline point on a centreline along a main direction of the target vessel and a predetermined number k of surrounding points surrounding each centreline point in form of a sphere with the respective centreline point in the centre of the respective sphere at each iteration i. The first deduction layer is arranged and configured to generate first current hidden states $h_{1,i}$, $h_{1,i}^k$ based on the provided one vessel shape point including the respective centreline point and the k surrounding points surrounding the centreline point and on the provided flow profile at the first iteration i=1 or provided first previous hidden states $h_{1,i-1}$, $h_{1,i-1}^k$ of the first deduction layer at any iteration subsequent to the first iteration i>1. The optional at least one further deduction layer is arranged and configured to generate at least one set of further current hidden states $h_{j,i}$, $h_{j,i}^k$ based on the current hidden states $h_{j-1,i}$, $h_{j-1,i}^k$ of the previous deduction layer and on initial states $s_{j,1}$, $s_{j,1}^k$ of the at least one further deduction layer at the first iteration i=1 or provided further previous hidden states $h_{j,i-1}$, $h_{j,i-1}^k$ of the at least one further deduction layer 13.j at any iteration subsequent to the first iteration i>1. The last deduction layer is arranged and configured to generate the last current hidden states $h_{M,i}$, $h_{M,i}^k$ based on the current hidden states $h_{M-1,i}$, $h_{M-1,i}^k$ of the previous deduction layer and on either initial states $s_{M,1}$, $s_{M,1}^k$ of the last deduction layer at the first iteration i=1 or provided last previous hidden states $h_{M,i-1}$, $h_{M,i-1}^k$ of the last deduction layer at any iteration subsequent to the first iteration i>1. The output block is arranged and configured to determine the at least one hemodynamic parameter $p_k$ based at least on the last generated current hidden states $h_{M,i}$, $h_{M,i}^k$.

The k surrounding points form the sphere that surrounds each centreline point along the centreline. The sphere has a predetermined radius c from each centreline point to a (spherical) surface of the sphere. Each surrounding point may have the same distance between itself and its neighbouring surrounding points or rather the respective centreline point. Each centreline point is preferably surrounded by 50 to 100 surrounding points (k∈[50; 100]).

Based on the current vessel shape point including the current centre line point and the k surrounding points surrounding the current centreline point as first input, the first input block provides information to the deduction block. Additionally, the second input block provides information based on the (inlet) flow profile to the deduction block at the first iteration i=1 or rather at the first vessel shape point of the provided vessel shape model of the target vessel including the current centre line point and the k surrounding points surrounding the current centreline point. In the deduction block, the provided information is transformed into first hidden states $h_{1,i}$, $h_{1,i}^k$ for the current iteration i by the first deduction layer. A first memory cell of the first deduction layer remembers the first current hidden states $h_{1,i}$, $h_{1,i}^k$ of the first deduction layer. These first current hidden states $h_{1,i}$, $h_{1,i}^k$ are used in the subsequent iteration i+1. There may be further deduction layers consecutively communicatively connected to the first deduction layer using the first current hidden states $h_{1,i}$, $h_{1,i}^k$ for deducing further current hidden states $h_{j,i}$, $h_{j,i}^k$. The last deduction layer uses the first current hidden states $h_{1,i}$, $h_{1,i}^k$, if there are no further deduction layers between the first deduction layer and the last deduction layer of the deduction block (M=2), or rather the last of the further current hidden states $h_{m-1,i}$, $h_{M-1,i}^k$ provided by the last further deduction layer, if there are further deduction layers between the first deduction layer and the last deduction layer of the deduction block (M>2), to derive the last current hidden states $h_{M,i}$, $h_{M,i}^k$.

Each deduction layer has memory cells having predefined initial states $s_{j,1}$, $s_{j,1}^k$ at the beginning of the iteration. For each iteration 1>1 after the first iteration i=1 the second input block receives no flow profile as second input for the deduction block. Instead the deduction layers use, besides the current vessel shape point including the current centre line point and the k surrounding points surrounding the current centreline point provided as first input via the first input block, the respective previous hidden states $h_{j,i-1}$, $h_{j,i-1}^k$ of itself at the previous iteration i-1 as additional input. The previous hidden states $h_{j,i-1}$, $h_{j,i-1}^k$ are remembered by the respective memory cells of the corresponding deduction layer and replace the respective initial sates $s_{j,1}$, $s_{j,1}^k$ after the first iteration i=1. At the first iteration each memory cell of each deduction layer has the predetermined initial state $s_{j,1}$, and $s_{j,1}^K$, which are used, except by the first deduction layer, in deriving the current hidden states $h_{j,i}$, $h_{j,i}^k$. These initial states $s_{j,1}$, $s_{j,1}^k$ of the memory cells of the deduction layers (except of the first deduction layer) can be seen as some sort of second input like the previous hidden states $h_{j,i-1}$, $h_{j,i-1}^k$, in the following iterations i>1.

Based on the last hidden states $h_{M,i}$, $h_{M,i}^k$ of each iteration i the output block determines the at least one hemodynamic parameter $p_k$ at the respective vessel shape point of the present iteration i.

A deduction block with a first and last deduction layer and optionally further deduction layers there between using vessel shape points including one centreline point and k surrounding points provides for most precise predictions of the at least one hemodynamic parameter along a target vessel and its bifurcations.

According to a refinement of at least one embodiment of the present invention the flow profile comprises an inlet blood flow velocity u in a direction x of a corresponding image dataset, an inlet blood flow velocity v in a direction y of the image dataset orthogonal to the direction x, and an inlet blood flow velocity w in a direction z of the image dataset orthogonal to the directions x and y. The flow profile further comprises optionally further information derived from at least one of the inlet blood flow velocities u, v, w and optionally boundary conditions like input flow rate, output flow rate etc.

The flow profile, in particular the flow profile at the inlet of the target vessel, may be derived from the corresponding image dataset which may have been recorded by a medical imaging system like a Computer Tomography (CT) device or a Magnet Resonance Imaging (MRI) device. The image dataset is a three-dimensional (3D) dataset with an inherent Cartesian coordinate system with orthogonal main directions x, y, z. The (inlet) flow profile which is used as second input to the AI unit comprises the three blood flow velocities u, v, w in the main directions x, y, z.

The three blood flow velocities u, v, w or rather the three Cartesian directions x, y, z may be transformed into a different coordinate system. For example, the Cartesian directions x, y, z could be transformed into radial coordinates with path s along the centreline, radius r from the centreline and angle φ and the velocities u, v, w could be correspondingly transformed into a longitudinal velocity, a radial velocity and a tangential velocity.

Additionally, further information like a secondary flow degree may be derived from the velocities u, v, w and included into the (inlet) flow profile.

The (inlet) flow profile provides for the initial conditions for predicting the at least one hemodynamic parameter in a very efficient way.

According to a refinement of at least one embodiment of the present invention the vessel shape model is derived from an image dataset, preferably generated by a medical imaging system, and most preferably from a four-dimensional, 4D, Magnetic Resonance Imaging, MRI, flow dataset generated by a 4D MRI system.

The coordinates x, y, z as well as the radius r of the target vessel can be directly provided from the image dataset without any previous transformation. Thus, the vessel shape model and in particular the vessel shape points can be provided very efficiently.

According to a refinement of at least one embodiment of the present invention the flow profile is derived from an image dataset, preferably generated by a medical imaging system, and most preferably from a 4D MRI flow dataset generated by a 4D MRI system.

In particular from the 4D MRI flow dataset the blood flow velocities u, v, w of the (inlet) flow profile can be directly provided without any previous transformation. The (inlet) flow profile or rather the blood flow velocities u, v, w are measured directly at the patient and, therefore, more accurate than any derived values. Further, the higher the quality of the 4D MRI flow dataset (cf. higher image quality) the more precise is the (inlet) flow profile/are the blood flow velocities u, v, w. Thus, the inlet flow profile can be provided very efficiently with very high precision.

According to a further refinement of at least one embodiment of the present invention the output block comprises: at least one concatenation layer and an output layer. The at least one concatenation layer is communicatively connected to the deduction block. The output layer is communicatively connected to the last of the at least one concatenation layer and to the deduction block. The at least one concatenation layer and the output layer are jointly arranged and configured to determine the at least one hemodynamic parameter $p_k$ based at least on the at least one generated current hidden state $h_{j,i}$.

The at least one concatenation layer may be a dense layer, a convolutional layer or the like. The at least one concatenation layer may comprise four to 256 nodes and preferably 48 nodes. The output block may comprise 1 to 10 concatenation layers.

The output layer may comprise one output node for every predicted hemodynamic parameter and preferably four output nodes.

For example, the at least one concatenation layer is communicatively connected to the last deduction layer of the deduction block, where preferably all nodes of the concatenation layer are connected to the nodes of the last deduction layer. The output layer is communicatively connected to the last of the at least one concatenation layer and to the last deduction layer of the deduction block, where preferably all output nodes of the output layer are connected with the nodes of the last of the at least one concatenation layer and also with the nodes of the last deduction layer.

Consequently, the output layer receives information form the last concatenation layer and additionally directly from the deduction block. in other words, the at least one concatenation layer and the output layer are jointly arranged and configured to determine the at least one hemodynamic parameter $p_k$ based at least on the last generated current hidden state $h_{m,\,i}$, which already implicitly contains all the information of the at least one hemodynamic parameter $p_k$.

The output block having at least one concatenation layer and one output layer enable fast, stable and precise deduction of the at least one hemodynamic parameter from the last hidden state of the deduction block.

According to a sixth embodiment of the present invention a computer-implemented method of training an Artificial Intelligence (AI) unit, preferably a Recurrent Neural Network (RNN) and most preferably a Long Short Term Memory (LSTM) network, as comprised by the AI system according to the second embodiment of the present invention comprises:

receiving an input training dataset comprising training vessel shape models and corresponding training flow profiles;

receiving an output training dataset corresponding to the received training input dataset comprising corresponding training hemodynamic parameters; and training the AI unit to predict at least one hemodynamic parameter $p_k$ of a target vessel with the received training vessel shape models and corresponding training flow profiles and the received set of corresponding training outputs.

According to a seventh embodiment of the present invention a computer program comprises instructions which, when the program is executed by a computer, cause the computer to carry out the steps of the method according to the embodiment aspect of the present invention.

According to an eighth embodiment of the present invention a computer-readable medium has stored thereon the computer program according to the seventh embodiment of the present invention.

According to a ninth embodiment of the present invention a data processing system comprises a device/apparatus for carrying out the steps of the method according to the sixth embodiment of the present invention.

A learning or rather training rule or paradigm, which is the basis of the present computer-implemented method of training the AI unit, is an algorithm which modifies the parameters of a respective Artificial Neural Network (ANN) like the AI unit, in order for a given input to the ANN to produce a favoured output. This training typically amounts to modifying the weights and thresholds of the variables within the ANN. Given a specific task to solve and a class of functions, learning means using a set of observations to find the one function of the class of functions, which solves the task in some optimal sense. This entails defining a cost function such that for the optimal solution the cost is minimal and no other solution has a cost less than the cost of the optimal solution. The cost function is an important concept in learning, as it is a measure of how far away a particular solution is from an optimal solution to the problem to be solved. Learning algorithms search through the solution space to find a function that has the smallest possible cost. For applications where the solution is data dependent, the cost must necessarily be a function of the observations, otherwise the model would not relate to the data. It is frequently defined as a statistic to which only approximations can be made. It is possible to define an arbitrary cost function, however, a particular cost function may be used either because it has desirable properties (e.g. convexity) or because it arises naturally from a particular formulation of the problem.

An ANN can be discriminatively trained with a standard backpropagation algorithm. Backpropagation is a method to calculate the gradient of a loss function (produces the cost associated with a given state) with respect to the weights in the ANN. The weight updates of backpropagation can be done via stochastic gradient descent. The choice of the cost function depends on factors such as the learning type (e.g. supervised, unsupervised, reinforcement etc.) and the activation function. Commonly, the activation function and cost function are the softmax function and cross entropy function, respectively.

In other words, training an ANN essentially means selecting one model from the set of allowed models (or, in a Bayesian framework, determining a distribution over the set of allowed models) that minimizes the cost. Commonly some form of gradient descent is deployed, using backpropagation to compute the actual gradients. This is done by simply taking the derivative of the cost function with respect to the network parameters and then changing those parameters in a gradient-related direction. Backpropagation training algorithms fall into three categories: steepest descent (with variable learning rate and momentum, resilient backpropagation), quasi-Newton (Broyden-Fletcher-Goldfarb-Shanno, one step secant), Levenberg-Marquardt and conjugate gradient (Fletcher-Reeves update, Polak-Ribiére update, Powell-Beale restart, scaled conjugate gradient).

Common training paradigms include supervised learning, unsupervised learning and reinforcement learning. Supervised learning uses a set of example pairs and the aim is to find a function in the allowed class of functions that matches the examples. In other words, the mapping implied by the data is inferred; the cost function is related to the mismatch between the mapping of the ANN and the data and it implicitly contains prior knowledge about the problem domain. The cost may be the mean-squared error, which tries to minimize the average squared error between the ANN's output and a target value over all the example pairs. Minimizing this cost using gradient descent for the class of ANNs called multilayer perceptrons (MLP), produces the backpropagation algorithm for training ANNs.

In unsupervised learning, some data is given and the cost function to be minimized that can be any function of the data and the ANN's output. The cost function is dependent on the task and any a priori assumptions (e.g. implicit properties or parameters of the model, observed variables etc.). In reinforcement learning, data is usually not given, but generated by an agent's interactions with the environment. At each point in time the agent performs an action and the environment generates an observation and an instantaneous cost according to some (usually unknown) dynamics.

The aim is to discover a policy for selecting actions that minimizes some measure of a long-term cost, e.g. the expected cumulative cost. The environment's dynamics and the long-term cost for each policy are usually unknown, but may also be estimated. The environment is commonly modelled as a Markov decision process (MDP) with states and actions with the following probability distributions: the instantaneous cost distribution, the observation distribution and the transition, while a policy is defined as the conditional distribution over actions given the observations. Taken together, the two then define a Markov chain (MC). The aim is to discover the policy (i.e., the MC) that minimizes the cost.

The AI unit is trained based on the input training dataset and the corresponding output data set. For sufficient training of the AI unit, such that at least one hemodynamic parameter $p_k$ can be reliably predicted based on the hidden states $h_{j,i}$ of a deduction block containing the actual AI network like the RNN or the LSTM network, the AI unit has to be trained with about at least 1000 different input training data sets and corresponding output datasets.

The received input training dataset comprises training vessel shape profiles and corresponding training flow profiles of vessels which are of the same type as the future target vessels for which the at least one hemodynamic parameter is to be predicted. For example, the input training data set may comprise training vessel shape models and corresponding flow profiles of aortas such that the trained AI unit is arranged and configured to predict at least one hemodynamic parameter $p_k$ for aortas as target vessels. The training vessel shape profiles and corresponding training flow profiles may be derived from image datasets acquired by a medical imaging system, preferably from 4D MRI flow datasets acquired by a 4D MRI system.

The received output training dataset comprises corresponding at least one hemodynamic parameter for each of the training vessel shape profiles and corresponding training flow profiles of the input training data set. The at least one training hemodynamic parameters may be derived from the same image datasets acquired by a medical imaging system, preferably from 4D MRI flow datasets acquired by a 4D MRI system as used for deriving the training vessel shape profiles and corresponding training flow profiles of the input training dataset.

The AI unit is consecutively provided with one training vessel shape profile and one corresponding training flow profile of the input training data set until all pairs of training vessel shape profile and one corresponding training flow profile of the input training data have been used for training the AI unit. During training, internal weights of the layers of the AI unit are adapted based on a difference of a current output of the AI unit compared to the corresponding training hemodynamic parameter of the output training dataset.

According to a refinement of an embodiment of the present invention the computer-implemented method comprises:

determining a shape variability and a geometric variability of a vessel within a given population by applying a statistical shape analysis on a set of real vessel shape models of the vessel;

synthesising at least one synthetic vessel shape model of the vessel based on the determined shape variability and geometric variability of the vessel within the given population;

determining the corresponding training flow profiles for the at least one synthetic vessel shape model and/or the set of real vessel shape models;

aggregating the input training dataset with the set of real shape models and optionally the at least one synthetic shape model as well as with the determined corresponding training flow profiles; and computing the corresponding at least one training hemodynamic parameters of the output training set based on the set of real shape models and/or the at least one synthetic vessel shape model as well as the corresponding flow profiles of the input training dataset.

The shape variability and the geometric variability of the vessel within the given population are determined via a data driven approach. A statistical shape analysis receives the set of real vessel shape models of the vessel, which may stem from or be based on image data sets of the vessel of different subjects from the given population generated with a certain or different medical imaging systems like Computer Tomography (CT) or MRI/4D MRI imaging systems. Via the statistical shape analysis a mean and variations of the shapes of the vessel in the given population are computed. Each of the variations may be interpreted as any human-defined shape definition (e.g. size, curvature, aortic length, width, height, etc.). For determining the shape variability and the geometric variability of the vessel within the given population preferably 50 to 500 and more preferably about 200 real vessel shape models of the vessel are used. For example, 194 real vessel shape models of the vessel (based on image datasets of 194 different subjects of the given population) are used for determining the shape variability and the geometric variability of the vessel (e.g. aorta) within the given population.

The at least one synthetic vessel shape model is later used for training the AI unit. Preferably there are 500 to 10,000 synthetic vessel shape models synthesised and most preferably there are about 800 to 1,000 synthetic vessel shape models synthesised based on the determined shape variability and geometric variability of the vessel within the given population.

Optionally, at least one synthetic vessel shape model of each of at least two different vessel shape model types is synthesised. The at least two different vessel shape model types may in particular be a bicuspid inlet model type and a tricuspid inlet model type, preferably of an aorta. Each of the at least one synthetic vessel shape model of each of the at least two different vessel shape model types are synthesised based on corresponding different shape variabilities and geometric variabilities of the vessel within the given population (i.e. separate image datasets of the bicuspid and tricuspid vessel or rather aorta in the given population). The (same) AI unit can be trained with all synthetic vessel shape models of all the at least two different vessel shape model types (and also with al real vessel shape models of each of the at least two different vessel shape model types), such that the trained AI unit can predict the at least one hemodynamic parameter for all of corresponding at least two different vessel (shape) types (i.e. bicuspid and tricuspid vessels/ aortas).

The corresponding training flow profiles for the at least one synthetic vessel shape model (optionally of each of the at least two different shape model types) and/or the set of real vessel shape models can be determined by statistical methods like interpolation and/or extrapolation or by matching derived shape parameters of the real vessel shape models and/or the synthetic vessel shape models with shape parameters of given vessel shape models in the target population.

The flow profiles of at least a part of the set of real vessel shape models can be determined directly from an image dataset, preferably generated by a medical imaging system, and most preferably from a 4D MRI flow dataset generated by a 4D MRI system.

The input training dataset can be aggregated from the set of real vessel shape models and the at least one synthetic vessel shape model (of each of the at least two different shape model types) such that preferably 500 to 10,000 and most preferably about 1,000 (real and/or synthetic) vessel shape models in total are included in the input training data set. Corresponding to each (real/synthetic) vessel shape model the determined corresponding flow profiles are included in the input training dataset, too.

Based on the aggregated input data set, the corresponding at least one training hemodynamic parameter for each real and/or synthetic vessel shape model with the corresponding flow profile of the input data set is determined, preferably by physical computations. The at last one training hemodynamic parameter for each (real/synthetic) vessel shape model with corresponding flow profile of the input training dataset form the output training dataset.

As there is only a limited number of image datasets of the vessel (e.g. aorta) for which the AI unit is to be trained available for training, the total number of vessel shape models in the training input dataset can be sufficiently increased by deriving synthetic vessel shape models based on the available real vessel shape models. Consequently, training of the AI unit with a sufficient number of real and synthetic vessel shape models is possible such that the trained AI unit can predict the at least one hemodynamic parameter for a target vessel with an accuracy that is sufficient for deduction of a diagnosis.

According to a refinement of an embodiment of the present invention the training hemodynamic parameters of the output training set are computed using Computational Fluid Dynamic (CFD) simulations.

With CFD simulations the training hemodynamic parameters of the output training set are determined with high precision and, thus, the AI unit trained based on these training hemodynamic parameters can predict the at least one hemodynamic parameter for the target vessel with high accuracy. This enables reliable diagnosis by a clinician and/or CDS system based on the predicted at least one hemodynamic parameter.

In FIG. 1 an embodiment of the method of predicting hemodynamic parameters according to the first aspect of the present invention is exemplarily depicted. The method comprises the steps of receiving 1 a vessel shape model, receiving 2 a corresponding flow profile and predicting 3 at least one hemodynamic parameter pk.

In the step of receiving 1 the vessel shape model of a target vessel, which here exemplarily is an aorta of a human subject, is received as first input. The vessel shape model has been extracted from an image dataset generated by a medical imaging system (e.g. 4D MRI flow dataset generated by a 4D MRI system) showing the aorta of the subject. The vessel shape model comprises a centreline extending from an inlet to an outlet of the aorta. The centreline runs through all centre points along the aorta. The vessel shape model comprises a multitude of N=100 vessel shape points each having a first coordinate in a first direction x, a second coordinate in a second direction y perpendicular to the first direction x and a third coordinate in a third direction z perpendicular to the first direction x and the second direction y. The vessel shape points of the vessel shape model lay on the centreline of the aorta and comprise a radius r of the aorta at the respective position of the vessel shape point along the centreline. Additionally, each vessel shape point may contain further information (e.g. change of radius of the aorta, position along the centreline, etc.).

In the step of receiving 2 the corresponding inlet flow profile of the aorta is received as second input. The corresponding flow profile of the aorta comprises the blood flow velocities u, v, w in the directions x, y, z at the inlet of the aorta, secondary flow degrees derived from the blood flow velocities x, y, z and boundary conditions, namely an input flow rate and an output flow rate at the inlet of the aorta. The inlet flow profile has been derived from the same image dataset as the vessel shape model.

In the step of predicting 3 four hemodynamic parameters p1, p2, p3, p4 of the aorta (e.g. a systolic blood pressure, a diastolic blood pressure, an arterial blood pressure, a mean arterial pressure, a systolic pressure variation, a pulse pressure variation, a stroke volume variation, a right atrial pressure, a right ventricular pressure, a pulmonary artery pressure, a mean pulmonary artery pressure, a pulmonary artery wedge pressure, a left arterial pressure, a cardiac output, a cardiac index, a stroke volume, a systemic vascular resistance, a systemic vascular resistance index, a pulmonary vascular resistance, a pulmonary vascular resistance index, a left ventricular stroke work, a left ventricular stroke work index, a right ventricular stroke work, a right ventricular stroke work index, a coronary artery perfusion pressure, a right ventricular end-diastolic volume, a right ventricular end-systolic volume, a right ventricular ejection fraction, etc.) are predicted by the AI unit at one of the vessel shape points of the vessel shape model.

The step of predicting 3 is iteratively executed for each consecutive vessel shape point of the received vessel shape model of the aorta starting from the inlet to an outlet of the aorta. In other words, for every vessel shape point (1 . . . N, N=100) of the provided vessel shape model of the aorta the four hemodynamic parameters $p_1$, $p_2$, $p_3$, $p_4$ are predicted in one iteration i, where i=1 . . . N and N=100. The received vessel shape model of the aorta is the first input that is used to predict the hemodynamic parameters $p_k$ (here k=1 . . . 4) of the aorta. The received corresponding inlet flow profile of the aorta is the second input that is used to predict the hemodynamic parameters $p_k$ (here k=1 . . . 4) of the aorta. The four hemodynamic parameters $p_1$, $p_2$, $p_3$, $p_4$ are predicted based on the information and features contained in the received vessel shape model and the corresponding inlet flow profile of the aorta. In particular, the four hemodynamic parameters are predicted by the AI unit each vessel shape point of the vessel shape model based on the three coordinates x, y, z of the vessel shape points and the respective radii r of the aorta as well as on the features of the flow profile (blood flow velocities u, v, w, derived secondary flow degrees and boundary conditions) at the inlet of the aorta. Here the AI unit exemplarily is an Artificial Neural Network (ANN) that is trained for predicting the hemodynamic parameters $p_k$ (k=1 . . . 4) of the aorta based on the vessel shape model and the corresponding inlet flow profile (of the aorta.

Each of the vessel shape points is iteratively stepped from the first vessel shape point to a last vessel shape point (along the centreline) of the received vessel shape model of the aorta. For each vessel shape point the four hemodynamic parameters $p_1$, $p_2$, $p_3$, $p_4$ are predicted by the AI unit, where for the first vessel shape point (at the first iteration i=1) the inlet flow profile and for any succeeding vessel shape point (at any other iteration i>1) the internal information of the AI unit at the preceding vessel shape point is used as second input.

Figure 2:
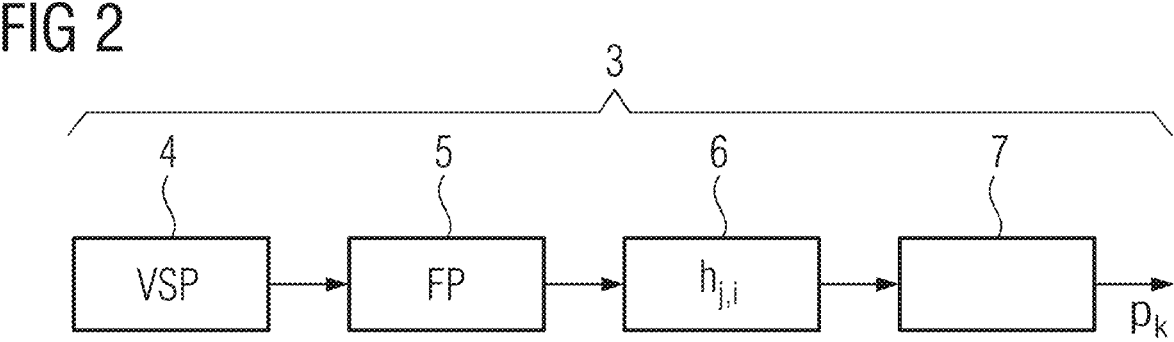
FIG. 2 shows a schematic flow chart of a further embodiment of the method of predicting hemodynamic parameters according to the first aspect of the present invention.

In FIG. 2 a further embodiment of the method of predicting hemodynamic parameters according to the first aspect of the present invention is exemplarily depicted. The method comprises the same steps (not depicted) as the embodiment of FIG. 1. Further, the step of determining 3 comprises the iterative (sub-)steps of providing 4 one vessel shape point, providing 5 the received flow profile, generating 6 at least one current hidden state $h_{j,i}$ and determining 7 the at least one hemodynamic parameter $p_k$.

The steps of providing 4, providing 5, generating 6 and determining 7 are iteratively executed for every vessel shape point 1 . . . N, N=100, of the received vessel shape model of the aorta.

At each iteration i=1 . . . N, N=100, in the step of providing 4 one (consecutive) vessel shape point of the received vessel shape model is provided to a first input block of the AI unit as first input.

Only at the first iteration i=1 in the step of providing 5 the received inlet flow profile is provided to a second input block of the AI unit as second input.

The information contained in the vessel shape point provided to the first input block and the information contained in the inlet flow profile provided to the second input block are transformed by the respective input blocks into features and provided to the deduction block.

At each iteration i=1 . . . N, N=100, in the step of generating 6 exemplarily two current hidden states $h_{1,i}$, $h_{M,i}$ (M=2) are generated in a deduction block of the AI unit. The deduction block here exemplarily comprises two deduction layers j=1 . . . N, N=2. The two current hidden states $h_{1,i}$, $h_{M,i}$ of the two deduction layers of the deduction block are generated based on the provided one vessel shape point or rather the provided features from the first input block as first input and at the first iteration i=1 based on the provided flow profile or rather the provided features from the second input block or at any iteration i>1 subsequent to the first iteration based on two respective previous hidden states $h_{1,i-1}$, $h_{M,i-1}$ of the deduction block as second input.

At each iteration i=1 . . . N, N=100, in the step of determining 7 the four hemodynamic parameters $p_1$, $p_2$, $p_3$, $p_4$ are determined as an output block of the AI unit. The last hidden state $h_{M,i}$ (here M=2) of the second/last deduction layer in each iteration contains all the information of the hemodynamic parameters $p_k$ (k=1 . . . 4) at the current vessel shape point. The information of the last hidden state $h_{2,i}$ is concatenated and combined in the output block into the four hemodynamic parameters $p_1$, $p_2$, $p_3$, $p_4$ at the current vessel shape point.

At the first iteration i=1 for the first vessel shape point the first deduction layer j=1 receives features from the first input block (transformed information of the first vessel shape point) and from the second input block (transformed information of the inlet flow profile). The first deduction layer j=1 generates the first current hidden state based on the features from the first and second input block. The second or here the last deduction layer has a predefined initial state $s_{M,1}$ (here exemplarily all nodes of the deduction layer are set to 0). Based on the current hidden state $h_{1,1}$ of the first deduction layer and on the initial state $s_{M,1}$ the second/last deduction layer generates the second or rather last current hidden state $h_{2,1}$. The information contained in the last hidden state $h_{M,1}$ is concatenated and combined by the output layer into the four hemodynamic parameters $p_1$, $p_2$, $p_3$, $p_4$ at the first vessel shape point At each iteration i=2 . . . N, N=100, subsequent to the first iteration the steps of providing 4, providing 5, generating 6 and determining 7 are executed in the same way, except that each deduction layer of the deduction block receives the respective previous hidden state $h_{1,i-1}$, $h_{M,i-1}$ as second input.

Figure 3:
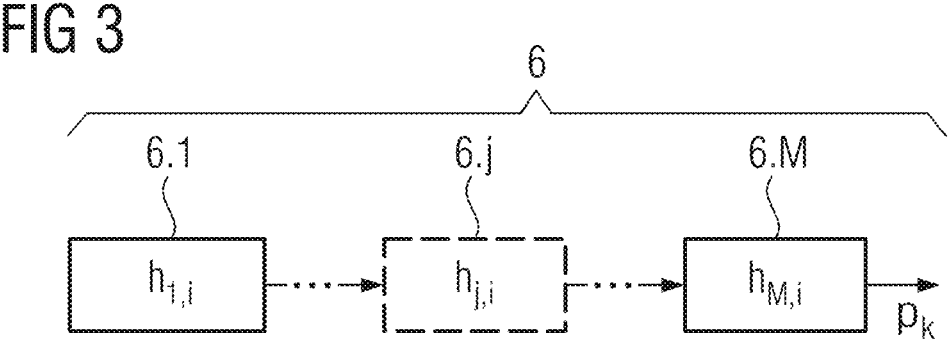
FIG. 3 shows a schematic flow chart of a further embodiment of the method of predicting hemodynamic parameters according to the first aspect of the present invention.

In FIG. 3 a further embodiment of the method of predicting hemodynamic parameters according to the first aspect of the present invention is exemplarily depicted. The method comprises the same steps (not depicted) as the embodiments of FIG. 1 and FIG. 2. Further, the step of generating 6 comprises the iterative (sub-)steps of generating 6.1 a first current hidden state $h_{1,i}$, generating 6.j at least one further current hidden state $h_{j,i}$ and generating 6.M the last current hidden state $h_{M,i}$.

The steps of generating 6.1, generating 6.j and generating 6.M are iteratively executed for every vessel shape point 1 . . . N, N=100, of the received vessel shape model of the aorta.

The deduction block of the AI unit comprises here exemplarily three deduction layers, the first deduction layer, one further deduction layer and the last deduction layer.

At each iteration i=1 . . . N, N=100, in the step of generating 6.1 the first deduction layer generates the first current hidden state h1, i of the first deduction layer. The generated first current hidden state h1, i is based on the provided one vessel shape point or rather the features provided by the first input block (transformed information of the provided vessel shape point) and based on the provided inlet flow profile or rather the features provided by the second input block (transformed information of the provided inlet flow profile) at the first iteration i=1 or a provided first previous hidden state h1, i−1 of the first deduction layer at any iteration i>1 subsequent to the first iteration.

At each iteration i=1 . . . N, N=100, in the step of generating 6.j (here j=2) the one further deduction layer generates the further current hidden state $h_{j,i}$ (here j=2) of the one further deduction layer. The generated further current hidden state $h_{j,i}$ is based on the first current hidden state $h_{1,i}$ of the first deduction layer and based on a predefined initial state $s_{j,1}$ (here j=2) of the one further deduction layer (here exemplarily all nodes of the deduction layer are set to 0) at the first iteration i=1 or a provided first previous hidden state $h_{j,i-1}$ of the one further deduction layer at any iteration i=2 . . . N subsequent to the first iteration.

At each iteration i=1 . . . N, N=100, in the step of generating 6.M (here M=3) the last deduction layer generates the last current hidden state $h_{M,i}$ (here M=3) of the last deduction layer. The generated last current hidden state $h_{M,i}$ is based on the further current hidden state $h_{j,i}$ of the one further deduction layer and based on a predefined initial state $s_{M,1}$ (here M=2) of the last deduction layer (here exemplarily all nodes of the deduction layer are set to 0) at the first iteration i=1 or a provided first previous hidden state $h_{j,i-1}$ of the one further deduction layer at any iteration i=2 . . . N subsequent to the first iteration.

In FIG. 4A an example vessel shape model 21 of the aorta 20 of the human subject is schematically depicted.

The vessel shape model 21 comprises consecutive vessel shape points 21.i (here exemplarily i=1 . . . 13 or 17, respectively) from the inlet of the aorta 20 (i=1) to the outlet of the aorta 20 (here exemplarily i=13 or 26, respectively). The vessel shape model 21 may be for only a predefined part of the aorta 20 of the human subject. The vessel shape model 21 may preferably comprise 50 to 500 and most preferably 100 consecutive vessel shape points from the inlet of the aorta 20 (i=1) to the outlet of the aorta 20 (i=N, preferably N∈[50; 500], most preferably N=100). The aorta 20 has a centreline CL that runs through all centreline points CLP.i of the aorta. Each vessel shape point 21.*i* comprises one of the centreline points CLP.i with corresponding coordinates x, y, z and further comprises a radius r.i of the aorta 20 orthogonal to the centreline CL at the respective centreline point CLP.i.

The vessel shape model 21 may be for a target vessel 20 like an aorta having more than one inlet and more than one outlet. Such vessel shape model 21 may comprise vessel shape points 21.*i* comprising centreline points CLP.i along several centrelines CL connecting the inlets with the outlets of the target vessel 20 (e.g. aorta) and running congruent in sections of the target vessel 20 or rather of the vessel shape model 21.

Figure 4B:
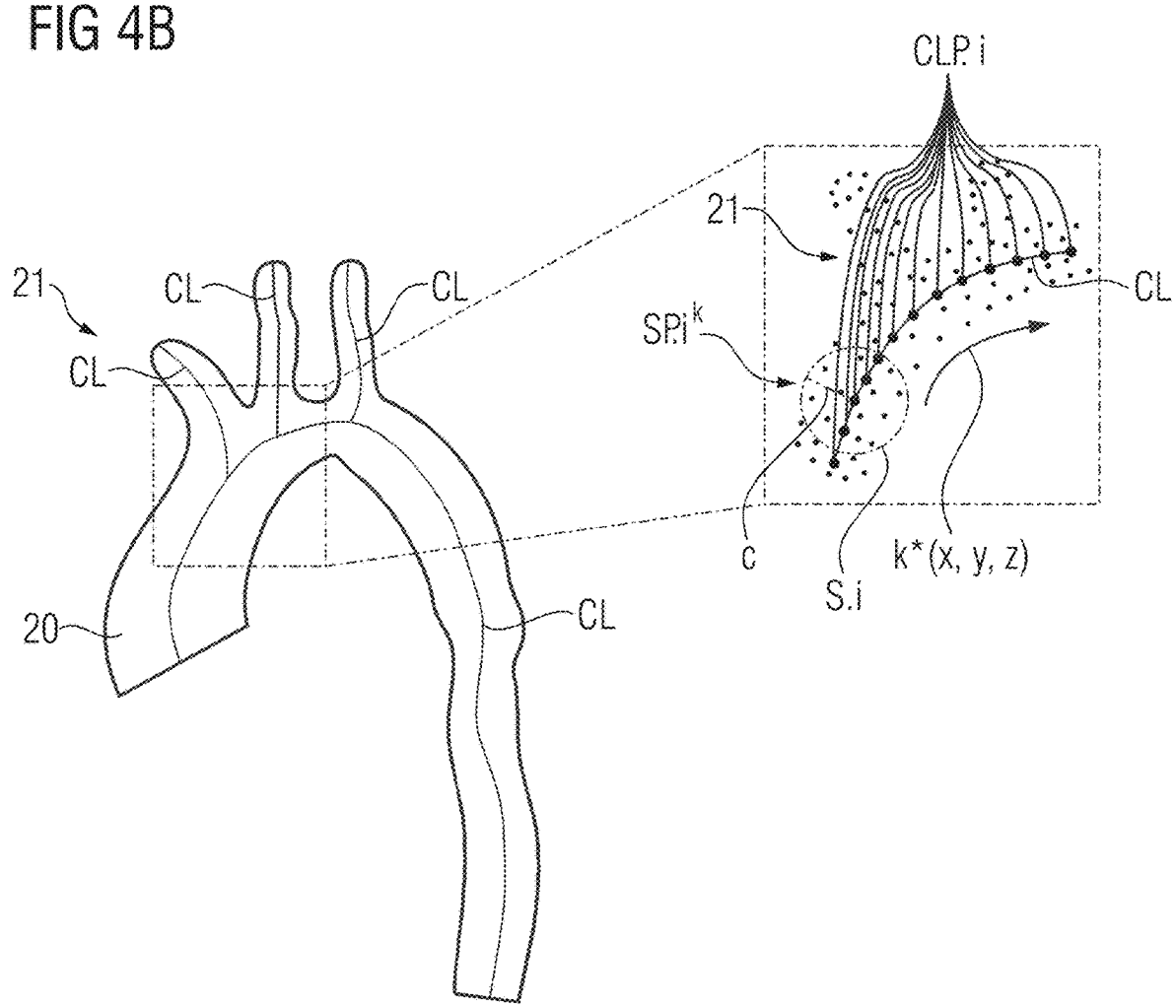
FIG. 4B shows a schematic view of another example vessel shape model of an aorta of a human subject.

In FIG. 4B another example vessel shape model 21 of the aorta 20 of the human subject is schematically depicted.

The vessel shape model 21 comprises consecutive vessel shape points 21.*i* (here exemplarily i=1 . . . 13 or 17, respectively) from the inlet of the aorta 20 (i=1) to the outlet of the aorta 20 (here exemplarily i=13 or 26, respectively). The vessel shape model 21 may be for only a predefined part of the aorta 20 of the human subject. The vessel shape model 21 may preferably comprise 50 to 500 and most preferably 100 consecutive vessel shape points from the inlet of the aorta 20 (i=1) to the outlet of the aorta 20 (i=N, preferably N∈[50; 500], most preferably N=100) and optionally also along bifurcations of the aorta. The aorta 20 has a centreline CL that runs through all centreline points CLP.i of the aorta and optionally also through the centreline of each bifurcation. Each vessel shape point 21.*i* comprises one of the centreline points CLP.i with corresponding coordinates x, y, z and further comprises a predefined number k of surrounding points SP.ik at the respective centreline point CLP.i. The k surrounding points SP.i surround the respective centreline point CLP.i in form of a sphere S.i with the respective centreline point CLP.i in the centre thereof. The sphere S.i of surrounding points has a radius c from the respective centreline point CLP.i to the surface of the sphere S.i.

The vessel shape model 21 may be for a target vessel 20 like an aorta having more than one inlet and more than one outlet. Such vessel shape model 21 may comprise vessel shape points 21.*i* comprising centreline points CLP.i along several centrelines CL connecting the inlets with the outlets of the target vessel 20 (e.g. aorta and bifurcations thereof) and running congruent in sections of the target vessel 20 or rather of the vessel shape model 21.

Figure 5:
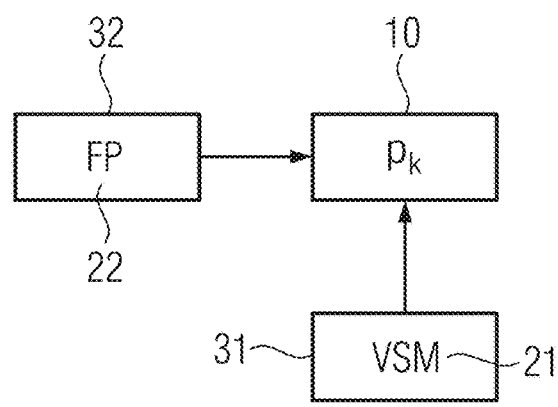
FIG. 5 shows a schematic view of an embodiment of the Artificial Intelligence (AI) system for predicting hemodynamic parameters according to the second aspect of the present invention.

In FIG. 5 an embodiment of the Artificial Intelligence (AI) system 30 for predicting hemodynamic parameters according to the second aspect of the present invention is schematically depicted. The AI system 30 is arranged and configured to execute the method of predicting hemodynamic parameters according to the first aspect or embodiment of the present invention. The AI system 30 comprises a first interface 31, a second interface 32 and an AI unit 10.

The first interface 31 and the second interface 32 are communicatively connected to the AI unit 10. The vessel shape model (VSM) 21 of the target vessel (e.g. an aorta of a human subject) is provided as first input via the first interface 31 of the AI system 30. The corresponding flow profile (FP) 22 of the target vessel is provided as second input via the second interface 32 of the AI system 30. The first input (VSM) and second input (FP) are forwarded to the AI unit 10 of the AI system 30. Based on the forwarded vessel shape model as first input and the flow profile as second input the AI unit 10 predicts the at least one hemodynamic parameter $p_k$ (e.g. four hemodynamic parameters $p_1$, $p_2$, $p_3$, $p_4$).

Figure 6:
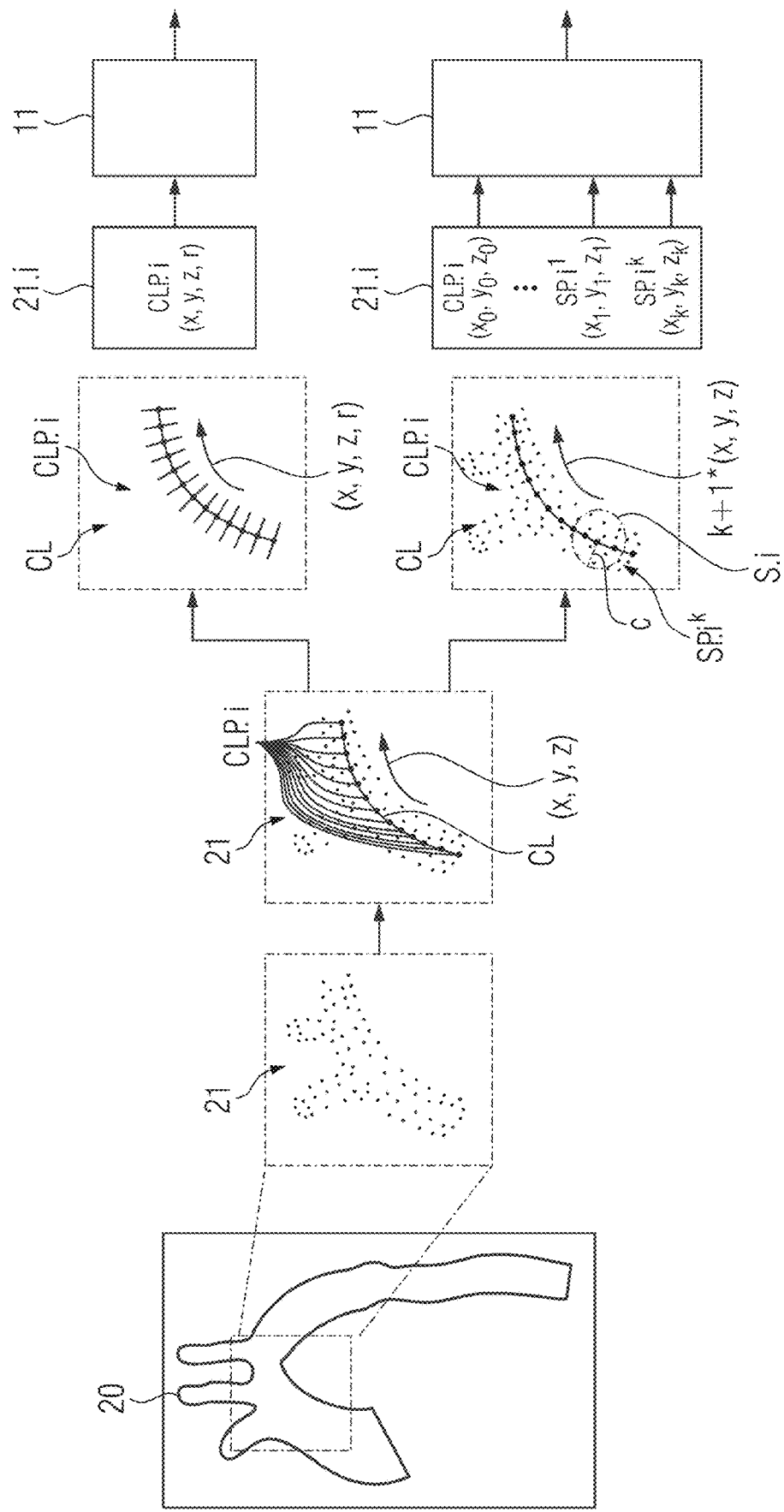
FIG. 6 shows a schematic view of refined embodiments of the AI system for predicting hemodynamic parameters according to the second aspect of the present invention.

In FIG. 6 refined embodiments of the AI system 30 for predicting hemodynamic parameters according to the second aspect or embodiment of the present invention are schematically depicted. The AI systems depicted in FIG. 6 comprise the same elements as the AI system of FIG. 5.

A vessel shape model (VSM) 21 of the target vessel 20 may be derived from medical images taken with medical imaging systems like 4D MRI, Computer Tomography (CT) or the like. The vessel shape model is here a 3D point cloud. The 3D point cloud 21 may comprise 10,000 to 100,000 points, preferably 40,000 points.

Based on the 3D point cloud a centreline CL along the target vessel, in particular along the main vessel and its bifurcations, can be computed. For example, from the 3D point cloud first a surface model of the target vessel 20 may be derived. Then, the surface model can be used to determine the centreline CL of the target vessel, i.e. of the aorta and its bifurcations.

The centreline CL comprises several consecutive centreline points CLP.i. Each centreline point CLP.i includes three coordinates x, y, z in the vessel shape model, i.e. the 3D point cloud.

The vessel shape model 21 comprises several vessel shape points (VSP) 21.*i* for each of which at least one hemodynamic parameter $p_k$ is predicted.

As schematically depicted in the upper branch of FIG. 6 (cf. FIG. 4A), each vessel shape point 21.*i* comprises one of the consecutive centreline points CLP.i and a respective radius r of the target vessel at the corresponding centreline point CLP.i. The vessel shape points 21.*i*, i.e. i times the coordinates x, y, z of the centreline points CLP.i and the respective radii r, are iteratively provided as input to a first input block 11 of the system 30 for predicting hemodynamic parameters (cf. FIG. 7).

Alternatively, as schematically depicted in the lower branch of FIG. 6 (cf. FIG. 4B), each vessel shape point 21.*i* comprises one of the consecutive centreline points CLP.i and several surrounding points SP.i, which surround each of the centreline points CLP.i. The surrounding points SP.ik of a centreline point CLP.i surround the latter in a sphere S.i with radius c. The vessel shape points 21.*i*, i.e. i times k+1 coordinates x, y, z of the centreline points CLP.i and the respective surrounding points SP.ik, are iteratively provided as input to a first input block 11 of the system 30 for predicting hemodynamic parameters (cf. FIG. 7).

Figure 7:
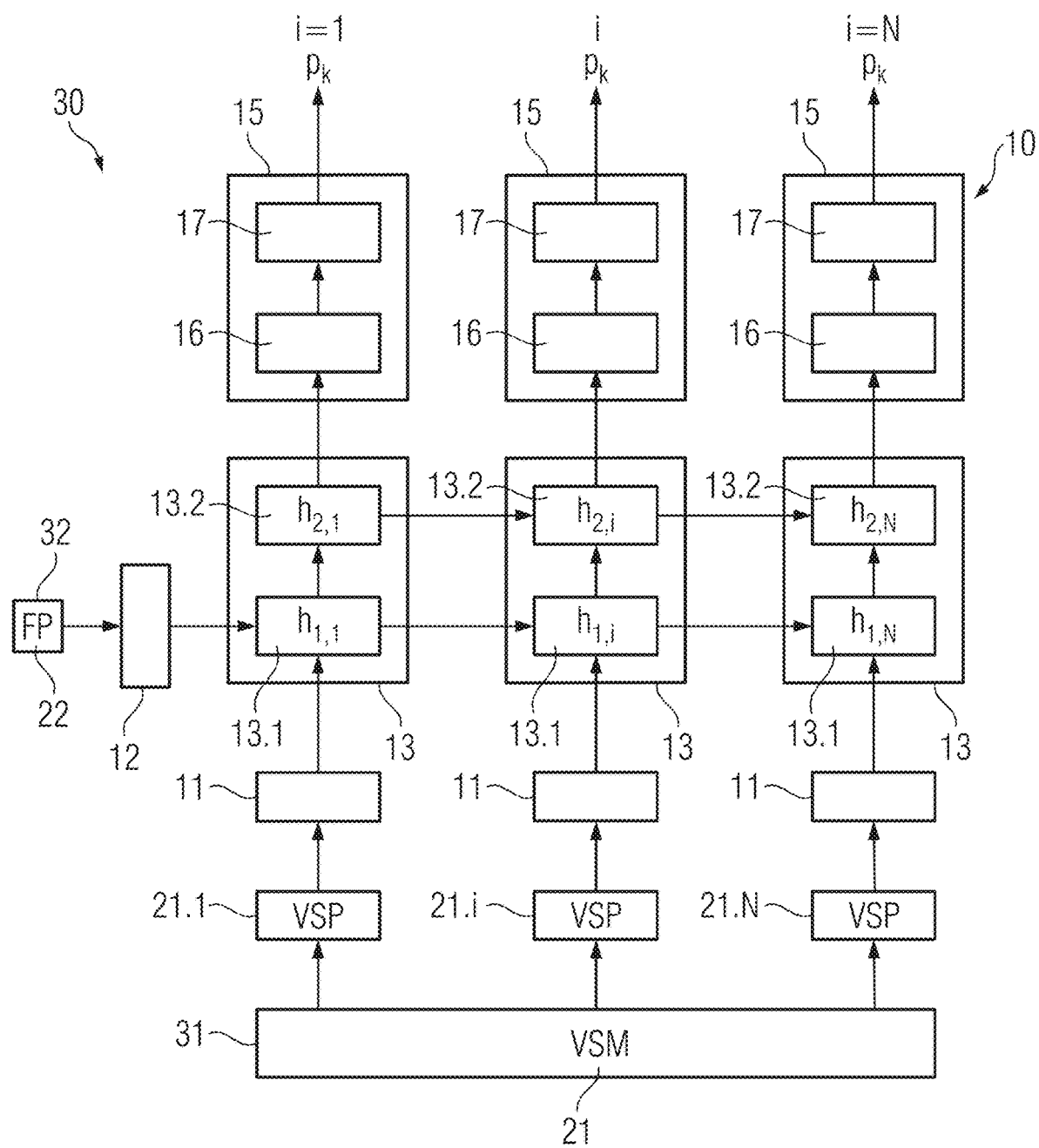
FIG. 7 shows another schematic view of the embodiments of the AI system for predicting hemodynamic parameters according to the second aspect of the present invention.

In FIG. 7 another schematic view of the embodiments of the AI system 30 for predicting hemodynamic parameters according to the second aspect or embodiment of the present invention is schematically depicted. The AI system depicted in FIG. 7 comprises the same elements as the AI system of FIGS. 5 and 6. Additionally, the AI unit 10 of the AI system 30 comprises a first input block 11, a second input block 12, a deduction block 13 and an output block 15.

The first input block 11 here exemplarily comprises one fully connected layer with 64 nodes. In case the vessel shape points 21.*i* provided to the first input block 11 each comprise one centreline point CLP.i and k surrounding points SP.i$^k$, the first input block exemplarily comprises one fully connected layer with k+1 times 64 nodes, namely 64 nodes for the centreline point CP.i and for each surrounding point SP.i$^k$. The second input block 12 here exemplarily comprises one fully connected layer with 64 nodes. The deduction block 13 here exemplarily comprises two (j=1 . . . M, M=2) fully connected deduction layers 13.1, 13.2 each with 64 nodes. In case the vessel shape points 21.*i* provided to the first input block 11 each comprise one centreline point CLP.i and k surrounding points SP.i$^k$, the deduction layers 13.1, 13.2 each comprise exemplarily k+1 times 64 nodes, namely 64 nodes for the centreline point CP.i and for each surrounding point SP.i$^k$. The output block 15 here exemplarily comprises one fully connected concatenation layer 16 with 48 nodes and one fully connected output layer 17 with four nodes, one node for each hemodynamic parameter $p_k$ (k=1 . . . 4) that is to be predicted by the AI unit 10. In case the deduction layers 13.1, 13.2 each comprise k+1 times 64 nodes, the output block comprises a one fully connected concatenation layer 16 with k+1 times 48 nodes and one fully connected output layer 17 with four nodes.

The first interface 31 is communicatively connected to the first input block 11 of the AI unit 10 and the second interface 32 is communicatively connected to the second input block 12 of the AI unit. The first input block 11 and the second input block 12 are communicatively connected to the first deduction layer 13.1 of the deduction block 13. The first deduction layer 13.1 is communicatively connected to the second or rather last deduction layer 13.2 of the deduction block 13. The second/last deduction layer 13.2 is communicatively connected to the concatenation layer 16 and to the output layer 17 of the output block 15. The concatenation layer 16 is communicatively connected to the output layer 17 of the output block.

In FIG. 7 there are exemplarily three iterations i=1 . . . N, N=3, depicted.

At each iteration i=1 . . . N, here N=3, the first input block 11 receives, staring from the inlet of the target vessel, one consecutive vessel shape point (VSP) 21.i of the vessel shape model 21 of the target vessel (e.g. aorta of the human subject) from the first interface 31. The first input block 11 transforms the information of the provided vessel shape point 21.i into features each represented by one node of the layer of the first input block 11.

At the first iteration i=1 the second input block 12 receives the (inlet) flow profile 22 from the second interface 32. The received (inlet) flow profile corresponds to the first vessel shape point 21.1 (at the inlet of the target vessel) received by the first input block 11. The second input block 12 transforms the information of the provided (inlet) flow profile 22 into features each represented by one node of the layer of the second input block 12. At any subsequent iteration i=2 . . . N, here N=3, there is no flow profile provided to the second input block.

At each iteration i=1 . . . N, here N=3, the first deduction layer 13.1 receives the features (transformed information of the current vessel shape point 21.i) from the first input block 11. Only at the first iteration i=1 the first deduction layer 13.1 receives the features (transformed information of the (inlet) flow profile 22) from the second input block 12. At any subsequent iteration i=2 . . . N, here N=3, the first deduction layer 13.1 receives a previous hidden state $h_{1,i-1}$ of the first deduction layer 13.1 from the previous iteration i−1. The first deduction layer 13.1 transforms the provided features into a current first hidden state $h_{1,i}$, or rather, in case the provided vessel shape points VSP.i each include one centreline point CLP.i and k surrounding points SP.i$^k$, a set of current first hidden states $h_{1,i}$, $h_{1,i}^k$, of the first deduction layer 13.1.

At each iteration i=1 . . . N, here N=3, the second/last deduction layer 13.2 receives the current first hidden state $h_{1,i}$, or rather, in case the provided vessel shape points VSP.i each include one centreline point CLP.i and k surrounding points SP.i$^k$, a set of current first hidden states $h_{1,i}$, $h_{1,i}^k$ from the first deduction layer 13.1. The second deduction layer 13.2 transforms the provided current first hidden state $h_{1,i}$, or rather set of current first hidden states $h_{1,i}$, $h_{1,i}^k$, and at the first iteration i=1 a predefined initial state $s_{2,1}$, or rather, in case the provided vessel shape points VSP.i each include one centreline point CLP.i and k surrounding points SP.i$^k$, a set of predefined initial states $s_{2,1}$, $s_{2,1}^k$, for the second/last deduction layer 13.2 or at any subsequent iteration i=2 . . . N, here N=3, a previous second or rather last hidden state or rather set of previous second or rather last hidden states $h_{2,i-1}$, $h_{2,i-1}^k$, of the second/last deduction layer 13.2 from the previous iteration i−1 into a current second/last hidden state $h_{2,i}$, or rather a set of current second/last hidden states $h_{2,i}$, $h_{2,i}^k$ of the second/last deduction layer 13.2.

At each iteration i=1 . . . N, here N=3, the concatenation layer 16 and also the output layer 17 of the output block receive the current second/last hidden state(s) $h_{2,i}$ ($h_{2,i}^k$) from the second/last deduction layer 13.2. The concatenation layer concatenates the current second/last hidden state $h_{2,i}$ ($h_{2,i}^k$) (64 features into 48 features, one for each of its nodes). The output layer 17 receives the current second/last hidden state (s) $h_{2,i}$ ($h_{2,i}^k$) from the second/last deduction layer 13.2 and the concatenated current second/last hidden state(s) (48 features (each)) from the concatenation layer 16 and derives the at least one hemodynamic parameter $p_k$ (here exemplarily four hemodynamic parameters $p_1$, $p_2$, $p_3$, $p_4$) for the current vessel shape point 21.i.

Figure 8:
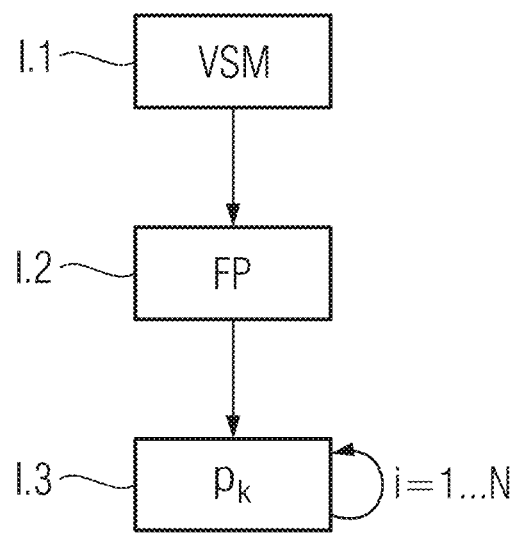
FIG. 8 shows a schematic view of an example algorithm of the computer program according to the third aspect of the present invention.

In FIG. 8 an example algorithm of the computer program according to the third aspect or embodiment of the present invention is schematically depicted. The computer program implements the method of predicting hemodynamic parameters according to the first aspect or embodiment of the present invention.

Based on a first instruction I.1 the computer program causes a computer system to execute the step of receiving a vessel shape model of the target vessel (e.g. an aorta of a human subject).

Based on a second instruction I.2 the computer program causes the computer system to execute the step of receiving a corresponding (inlet) flow profile of the target vessel.

Based on a third instruction I.3 the computer program causes the computer system to execute the step of predicting at least one hemodynamic parameter pk based on the received vessel shape model and the received flow profile by an AI unit.

Figure 9:
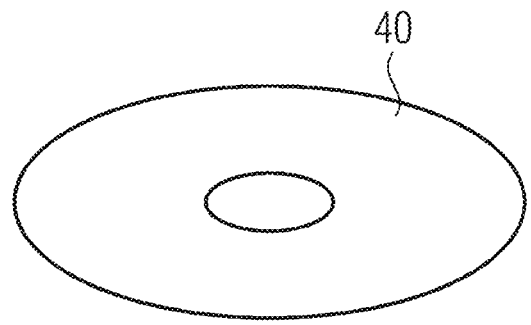
FIG. 9 shows a schematic view of an embodiment of the computer-readable medium according to the fourth aspect of the present invention.

In FIG. 9, an embodiment of the computer-readable medium 40 according to the fourth aspect or embodiment of the present invention is schematically depicted.

Here, exemplarily a computer-readable storage disc 40 like a Compact Disc (CD), Digital Video Disc (DVD), High Definition DVD (HD DVD) or Blu-ray Disc (BD) has stored thereon the computer program according to the third aspect of the present invention and as schematically shown in FIG. 7. However, the computer-readable medium 40 may also be a data storage like a magnetic storage/memory (e.g. magnetic-core memory, magnetic tape, magnetic card, magnet strip, magnet bubble storage, drum storage, hard disc drive, floppy disc or removable storage), an optical storage/memory (e.g. holographic memory, optical tape, Tesa tape, Laserdisc, Phasewriter (Phasewriter Dual, PD) or Ultra Density Optical (UDO)), a magneto-optical storage/memory (e.g. MiniDisc or Magneto-Optical Disk (MO-Disk)), a volatile semiconductor/solid state memory (e.g. Random Access Memory (RAM), Dynamic RAM (DRAM) or Static RAM (SRAM)), a non-volatile semiconductor/solid state memory (e.g. Read Only Memory (ROM), Programmable ROM (PROM), Erasable PROM (EPROM), Electrically EPROM (EEPROM), Flash-EEPROM (e.g. USB-Stick), Ferroelectric RAM (FRAM), Magnetoresistive RAM (MRAM) or Phase-change RAM).

Figure 10:
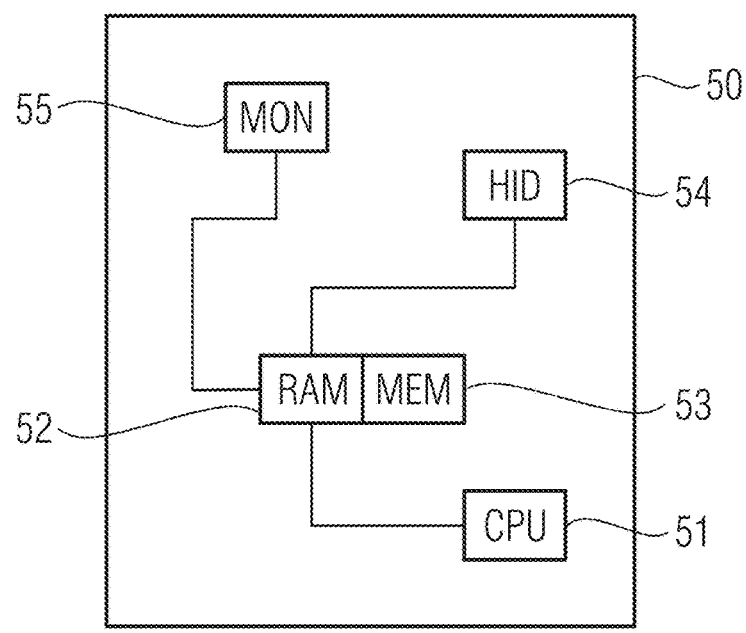
FIG. 10 shows a schematic view of an embodiment of the data processing system according to the fifth aspect of the present invention.

In FIG. 10 an embodiment of the data processing system 50 according to the fifth aspect or embodiment of the present invention is schematically depicted.

The data processing system 50 may be a personal computer (PC), a laptop, a tablet, a server, a distributed system (e.g. cloud system) and the like. The data processing system 50 comprises a central processing unit (CPU) 51, a memory having a random access memory (RAM) 52 and a nonvolatile memory (MEM, e.g. hard disk) 53, a human interface device (HID, e.g. keyboard, mouse, touchscreen etc.) 54 and an output device (MON, e.g. monitor, printer, speaker, etc.) 55. The CPU 51, RAM 52, HID 54 and MON 55 are communicatively connected via a data bus. The RAM 52 and MEM 53 are communicatively connected via another data bus.

The computer program according to the third aspect or embodiment of the present invention and schematically depicted in FIG. 7 can be loaded into the RAM 52 from the MEM 53 or another computer-readable medium 40. According to the computer program the CPU 51 executes the steps 1 to 3 of the method according to the first aspect or embodiment of the present invention and schematically depicted in FIGS. 1 to 3. The execution can be initiated and controlled by a user via the HID 54. The status and/or result of the executed computer program may be indicated to the user by the MON 55. The result of the executed computer program may be permanently stored on the non-volatile MEM 53 or another computer-readable medium.

In particular, the CPU 51 and RAM 53 for executing the computer program may comprise several CPUs 51 and several RAMs 53 for example in a computation cluster or a cloud system. The HID 54 and MON 55 for controlling execution of the computer program may be comprised by a different data processing system like a terminal communicatively connected to the data processing system 50 (e.g. cloud system).

Figure 11:
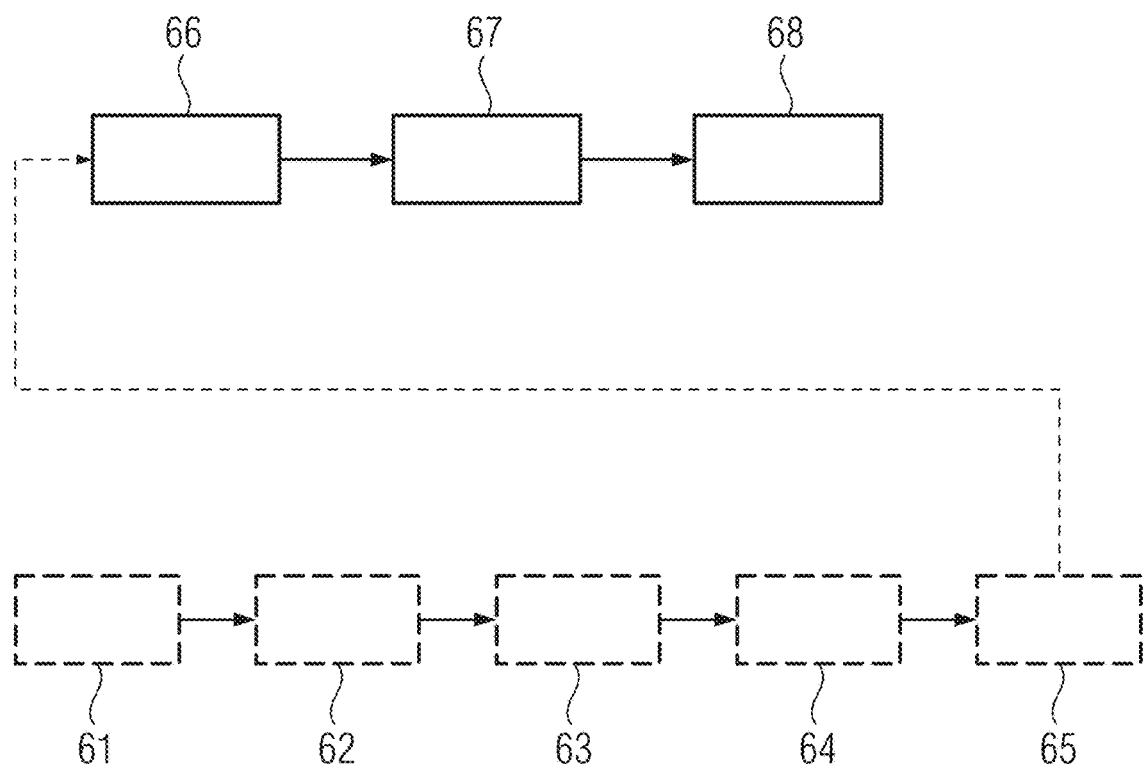
FIG. 11 shows a schematic flow chart of an embodiment of the computer-implemented method of training an Artificial Intelligence (AI) unit according to the sixth aspect of the present invention.

In FIG. 11 an embodiment of the computer-implemented method of training an AI unit according to the sixth aspect or embodiment of the present invention is schematically depicted. The computer-implemented method comprises the steps of receiving 66 an input training data set, receiving 67 an output training dataset and training 68 the AI unit. Optionally, the computer-implemented method further comprises the initial steps of determining 61 a shape variability and a geometric variability, synthesising 62 at least one synthetic vessel shape model, determining 63 the corresponding training flow profiles, aggregating 64 the input dataset and computing 65 the corresponding at least one hemodynamic parameter.

In the step of receiving 66 the input training dataset is received. The received input training dataset comprises training vessel shape profiles and corresponding training flow profiles of vessels, here of aortas of human subjects of a target population. The training vessel shape profiles and corresponding training flow profiles are of the same type of vessel as the future target vessels for which the at least one hemodynamic parameter (e.g. four hemodynamic parameters p1, p2, p3, p4) is to be predicted. The training vessel shape profiles and corresponding training flow profiles can be derived from image datasets acquired by a medical imaging system like from 4D MRI flow datasets acquired by a 4D MRI system.

In the step of receiving 67 the output training dataset is received. The received output data set comprises corresponding at least one training hemodynamic parameters for each of the training vessel shape profiles and corresponding training flow profiles of the input training data set (here exemplarily four training hemodynamic parameters for each). The at least one training hemodynamic parameters can be derived from the same image datasets acquired by the medical imaging system (e.g. from the 4D MRI flow datasets acquired by the 4D MRI system) as used for deriving the training vessel shape profiles and corresponding training flow profiles of the input training dataset.

In the step of training 68 the AI unit is consecutively provided with one training vessel shape profile and one corresponding training flow profile of the input training data set from the first to the last pair. During training 68 internal weights of the layers of the AI unit (here exemplarily one fully connected input layer with 64 nodes of a first input block, one fully connected input layer with 64 nodes of a second input block, two fully connected LSTM deduction layers with 64 nodes of a deduction block and a fully connected concatenation layer with 48 nodes as well as a fully connected output layer with 4 nodes of an output block) are adapted based on a difference of a current output of the (output layer of the) AI unit compared to the corresponding training hemodynamic parameter of the output training dataset. The trained AI unit is, after the training 68 has been completed, arranged and configured to predict four hemodynamic parameters $p_k$, k=1 . . . 4, for aortas as target vessels.

In the optional initial step of determining 61, the shape variability and the geometric variability of a vessel, here exemplarily the aorta, within a given population, here exemplarily 200 subjects, is determined by applying a statistical shape analysis on a set of real vessel shape models of the aorta. The shape variability and the geometric variability of the aorta within the given population are determined via a data driven approach, where the statistical shape analysis receives the set of real vessel shape models of the aorta. The real vessel shape models stem from or rather are based on image data sets of the aorta of the 200 subjects from the given population (e.g. 4D MRI flow datasets). Via the statistical shape analysis a mean and variations of the shapes of the aorta in the given population are computed.

In the optional initial step of synthesising 62 the at least one synthetic vessel shape model is synthesised based on the determined shape variability and geometric variability of the aorta within the given population. Exemplarily, here are 800 synthetic vessel shape models synthesised based on the determined shape variability and geometric variability of the aorta within the given population. Thereby there are synthetic vessel shape models of each of wo different vessel shape model types, a bicuspid and a tricuspid inlet model type of the aorta, synthesised. The synthetic vessel shape models of each of the two different vessel shape model types are synthesised based on corresponding different shape variabilities and geometric variabilities of the aorta with bicuspid valves and of the aorta with tricuspid valves within the given population. The AI unit is later trained with all synthetic vessel shape models of both different vessel shape model types, such that the trained AI unit can predict the four hemodynamic parameters pk, k=1 . . . 4, for bicuspid and tricuspid aortas.

In the step of determining 63 the corresponding training flow profiles for the 800 synthetic vessel shape models of the bicuspid and tricuspid shape model type and additionally or alternatively for the set of real vessel shape models are determined by a statistical method (e.g. interpolation and/or extrapolation or by matching derived shape parameters of the real vessel shape models and/or the synthetic vessel shape models with shape parameters of given vessel shape models in the target population). The flow profiles of at least a part of the set of real vessel shape models can alternatively be determined directly from the image dataset generated by the medical imaging system (e.g. the 4D MRI flow dataset generated by the 4D MRI system).

In the step of aggregating 64 the input training dataset is aggregated from the set of 200 real vessel shape models and the 800 synthetic vessel shape models of the bicuspid and tricuspid shape model type such that 1,000 (real and synthetic) vessel shape models in total are included in the input training data set. Corresponding to each (real/synthetic) vessel shape model the determined corresponding flow profiles are included in the input training dataset, too.

In the step of computing 65, the corresponding four training hemodynamic parameters for each of the 1,000 (real and synthetic) vessel shape models are computed for the output training dataset. Based on the aggregated input data set, namely the 1,000 (real and synthetic) vessel shape models and the corresponding flow profiles, the corresponding four training hemodynamic parameters for each (real and synthetic) vessel shape model with the corresponding flow profile of the input data set is determined by physical computations.

Figure 12:
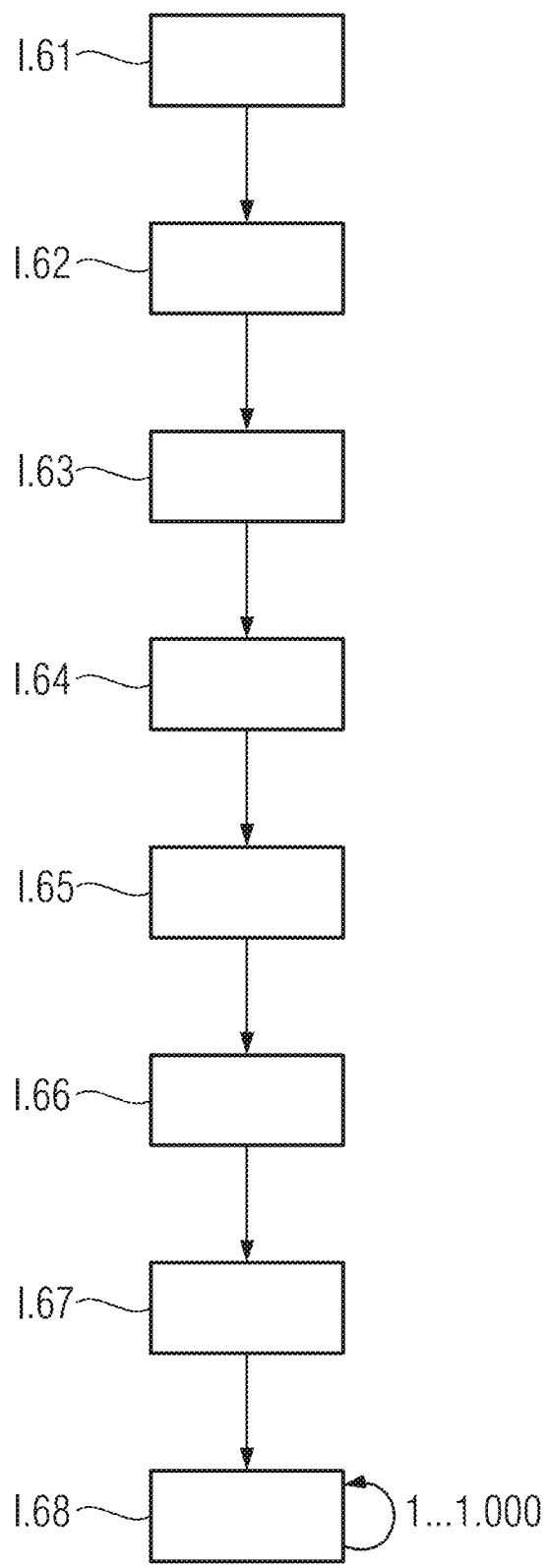
FIG. 12 shows a schematic view of an example algorithm of the computer program according to the seventh aspect of the present invention.

In FIG. 12 an example algorithm of the computer program according to the seventh aspect or embodiment of the present invention is schematically depicted. The computer program implements the computer-implemented method of training an AI unit according to the sixth aspect of the present invention.

Based on an optional first instruction I.61 the computer program causes a computer system to execute the step of determining a shape variability and a geometric variability of a vessel (e.g. the aorta) within a given population (e.g. 200 human subjects) by applying a statistical shape analysis on a set of real vessel shape models of the vessel.

Based on an optional second instruction I.62 the computer program causes the computer system to execute the step of synthesising at least one synthetic vessel shape model of the vessel based on the determined shape variability and geometric variability of the vessel within the given population.

Based on an optional third instruction I.63 the computer program causes the computer system to execute the step of determining corresponding training flow profiles for the at least one synthetic vessel shape model and/or for a set of real vessel shape models.

Based on an optional fourth instruction I.64 the computer program causes the computer system to execute the step of aggregating an input training dataset with the set of real shape models and optionally the at least one synthetic shape model as well as with the determined corresponding training flow profiles.

Based on an optional fifth instruction I.65 the computer program causes the computer system to execute the step of computing corresponding at least one training hemodynamic parameters (e.g. four hemodynamic parameters) of the output training set based on the set of real vessel shape models and/or the at least one synthetic vessel shape model as well as the corresponding flow profiles of the input training dataset.

Based on a sixth instruction I.66 the computer program causes the computer system to execute the step of receiving the input training dataset comprising the training vessel shape models and the corresponding training flow profiles.

Based on a seventh instruction I.67 the computer program causes the computer system to execute the step of receiving the output training dataset corresponding to the received training input dataset comprising the corresponding at least one (here exemplarily four) training hemodynamic parameters.

Based on an eighth instruction I.68 the computer program causes the computer system to execute the step of training the AI unit to predict at least one hemodynamic parameter pk (here four hemodynamic parameters p1, p2, p3, p4) of a target vessel (e.g. the aorta) with the received training vessel shape models and corresponding training flow profiles and the received set of corresponding training outputs.

Figure 13:
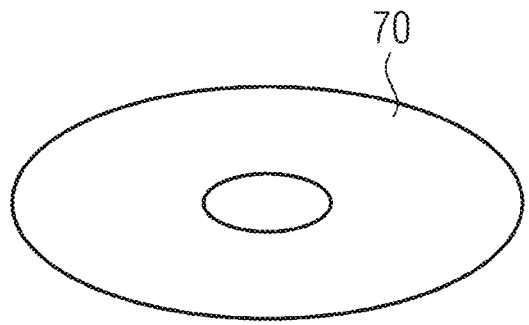
FIG. 13 shows a schematic view of an embodiment of the computer-readable medium according to the eighth aspect of the present invention.

In FIG. 13 an embodiment of the computer-readable medium 70 according to the eighth aspect or embodiment of the present invention is schematically depicted.

Here, exemplarily a computer-readable storage disc 70 like a Compact Disc (CD), Digital Video Disc (DVD), High Definition DVD (HD DVD) or Blu-ray Disc (BD) has stored thereon the computer program according to the seventh aspect or embodiment of the present invention and as schematically shown in FIG. 11. However, the computer-readable medium 70 may also be a data storage like a magnetic storage/memory (e.g. magnetic-core memory, magnetic tape, magnetic card, magnet strip, magnet bubble storage, drum storage, hard disc drive, floppy disc or removable storage), an optical storage/memory (e.g. holographic memory, optical tape, Tesa tape, Laserdisc, Phasewriter (Phasewriter Dual, PD) or Ultra Density Optical (UDO)), a magneto-optical storage/memory (e.g. MiniDisc or Magneto-Optical Disk (MO-Disk)), a volatile semiconductor/solid state memory (e.g. Random Access Memory (RAM), Dynamic RAM (DRAM) or Static RAM (SRAM)), a non-volatile semiconductor/solid state memory (e.g. Read Only Memory (ROM), Programmable ROM (PROM), Erasable PROM (EPROM), Electrically EPROM (EEPROM), Flash-EEPROM (e.g. USB-Stick), Ferroelectric RAM (FRAM), Magnetoresistive RAM (MRAM) or Phase-change RAM).

Figure 14:
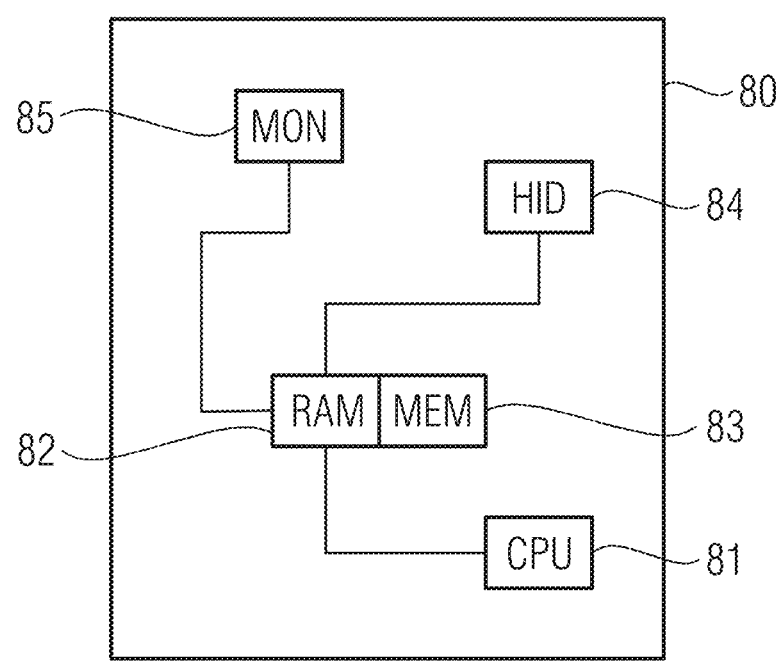
FIG. 14 shows a schematic view of an embodiment of the data processing system according to the ninth aspect of the present invention.

In FIG. 14 an embodiment of the data processing system 80 according to the ninth aspect or embodiment of the present invention is schematically depicted.

The data processing system 80 may be a personal computer (PC), a laptop, a tablet, a server, a distributed system (e.g. cloud system) and the like. The data processing system 80 comprises a central processing unit (CPU) 81, a memory having a random access memory (RAM) 82 and a nonvolatile memory (MEM, e.g. hard disk) 83, a human interface device (HID, e.g. keyboard, mouse, touchscreen etc.) 84 and an output device (MON, e.g. monitor, printer, speaker, etc.) 85. The CPU 81, RAM 82, HID 84 and MON 85 are communicatively connected via a data bus. The RAM 82 and MEM 83 are communicatively connected via another data bus. The computer program according to the seventh aspect or embodiment of the present invention and schematically depicted in FIG. 11 can be loaded into the RAM 82 from the MEM 83 or another computer-readable medium 70. According to the computer program the CPU 81 executes the steps 61 to 68 of the computer-implemented method according to the sixth aspect or embodiment of the present invention and schematically depicted in FIG. 11. The execution can be initiated and controlled by a user via the HID 84. The status and/or result of the executed computer program may be indicated to the user by the MON 85. The result of the executed computer program may be permanently stored on the non-volatile MEM 83 or another computer-readable medium.

In particular, the CPU 81 and RAM 83 for executing the computer program may comprise several CPUs 81 and several RAMs 83 for example in a computation cluster or a cloud system. The HID 84 and MON 85 for controlling execution of the computer program may be comprised by a different data processing system like a terminal communicatively connected to the data processing system 80 (e.g. cloud system).

Although specific embodiments have been illustrated and described herein, it will be appreciated by those of ordinary skill in the art that a variety of alternate and/or equivalent implementations exist. It should be appreciated that the example embodiment or example embodiments are only examples, and are not intended to limit the scope, applicability, or configuration in any way. Rather, the foregoing summary and detailed description will provide those skilled in the art with a convenient road map for implementing at least one example embodiment, it being understood that various changes may be made in the function and arrangement of elements described in an example embodiment without departing from the scope as set forth in the appended claims and their legal equivalents. Generally, this application is intended to cover any adaptations or variations of the specific embodiments discussed herein.

In the foregoing detailed description, various features are grouped together in one or more examples for the purpose of streamlining the disclosure. It is understood that the above description is to be illustrative, and not restrictive. It is intended to cover all alternatives, modifications and equivalents as may be included within the scope of the invention. Many other examples will be apparent to one skilled in the art upon reviewing the above specification.

Specific nomenclature used in the foregoing specification is used to provide a thorough understanding of the invention. However, it will be apparent to one skilled in the art in light of the specification provided herein that the specific details are not required in order to practice the invention. Thus, the foregoing descriptions of specific embodiments of the present invention are presented for purposes of illustration and description. They are not intended to be exhaustive or to limit the invention to the precise forms disclosed; obviously many modifications and variations are possible in view of the above teachings.

The embodiments were chosen and described in order to best explain the principles of the invention and its practical applications, to thereby enable others skilled in the art to best utilize the invention and various embodiments with various modifications as are suited to the particular use contemplated. Throughout the specification, the terms "including" and "in which" are used as the plain-English equivalents of the respective terms "comprising" and "wherein," respectively. Moreover, the terms "first," "second," and "third," etc., are used merely as labels, and are not intended to impose numerical requirements on or to establish a certain ranking of importance of their objects. In the context of the present description and claims the conjunction "or" is to be understood as including ("and/or") and not exclusive ("either . . . or").

Although the invention has been illustrated and described in greater detail with reference to the referred example embodiments, the invention is not restricted thereby. Other variations and combinations can be derived herefrom by the person skilled in the art without departing from the essential concept of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of predicting hemodynamic parameters for a target vessel, the method comprising:
   receiving a vessel shape model of the target vessel;
   receiving a flow profile corresponding to the target vessel; and
   iteratively predicting at least one hemodynamic parameter based on the vessel shape model and the flow profile, via an Artificial Intelligence (AI) unit, wherein
      the iteratively predicting the at least one hemodynamic parameter includes predicting the at least one hemodynamic parameter for a first vessel shape point based on the first vessel shape point and the flow profile and for a second vessel shape point based on the second vessel shape point and a hidden state of the first vessel shape point,
      the first vessel shape point and the second vessel shape point are consecutive vessel shape points of the vessel shape model, and
      the flow profile is an inlet flow profile for the target vessel at the first vessel shape point.

2. The method of claim 1, wherein the predicting includes:
   providing, to a first input block of the AI unit, the first vessel shape point of the vessel shape model;
   providing, to a second input block of the AI unit, the flow profile;
   generating at least one first current hidden state, in a deduction block of the AI unit, based on the first vessel shape point and on the flow profile;
   determining the at least one hemodynamic parameter for the first vessel shape point in an output block of the AI unit, based at least on the at least one first current hidden state;
   providing, to the first input block of the AI unit, the second vessel shape point of the vessel shape model;
   generating at least one second current hidden state, in the deduction block of the AI unit, based on the second vessel shape point and the at least one first current hidden state; and determining the at least one hemodynamic parameter for the second vessel shape point in the output block of the AI unit, based at least on a last generated current hidden state of the at least one second current hidden state.

3. The method of claim 2, wherein
the generating the at least one first current hidden state includes
generating a current hidden state of the at least one first current hidden state in a first deduction layer of the AI unit based on the first vessel shape point and the flow profile, and
generating a last current hidden state of the at least one first current hidden state in a last deduction layer of the AI unit based on the current hidden state of the at least one first current hidden state; and
the generating the at least one second current hidden state includes
generating a current hidden state of the at least one second current hidden state in the first deduction layer of the AI unit based on the second vessel shape point and the current hidden state of the at least one first current hidden state, and
generating a last current hidden state of the at least one second current hidden state in the last deduction layer based on the current hidden state of the at least one second current hidden state and the last current hidden state of the at least one first current hidden state.

4. The method of claim 1, wherein the vessel shape model includes a centerline along a main direction of the target vessel and wherein each of the consecutive vessel shape points includes a consecutive centerline point on the centerline and a radius of the target vessel at a respective centerline point.

5. The method of claim 2, wherein the vessel shape model includes a centerline along a main direction of the target vessel and wherein each of the consecutive vessel shape points includes a consecutive centerline point on the centerline and a number of surrounding points surrounding each centerline point in a form of a sphere with the respective centerline point in the center of the respective sphere, wherein,
the generating the at least one first current hidden state includes
generating a current hidden state of the at least one first current hidden state in a first deduction layer of the AI unit based on the first vessel shape point including the respective centerline point and the number of surrounding points surrounding the centerline point and on the flow profile, and
generating a last current hidden state of the at least one first current hidden state in a last deduction layer of the AI unit based on the current hidden state of the at least one first current hidden state; and
the generating the at least one second current hidden state includes
generating a current hidden state of the at least one second current hidden state in the first deduction layer of the AI unit based on the second vessel shape point including the respective centerline point and the number of surrounding points surrounding the centerline point and the current hidden state of the at least one first current hidden state, and
generating a last current hidden state of the at least one second current hidden state in the last deduction layer based on the current hidden state of the at least one second current hidden state and the last current hidden state of the at least one first current hidden state, and wherein, the determining the at least one hemodynamic parameter for the first vessel shape point determines the at least one hemodynamic parameter in the output block of the AI unit based on the last current hidden state of the at least one first current hidden state, and the determining the at least one hemodynamic parameter for the second vessel shape point determines the at least one hemodynamic parameter in the output block of the AI unit based on the last current hidden state of the at least one second current hidden state.

6. The method of claim 1, wherein the flow profile includes:
an inlet blood flow velocity u in a direction x of an image dataset;
an inlet blood flow velocity v in a direction y of the image dataset orthogonal to the direction x; and
an inlet blood flow velocity w in a direction z of the image dataset orthogonal to the directions x and y.

7. The method of claim 1, wherein at least one of the vessel shape model or the flow profile is derived from an image dataset.

8. An artificial intelligence (AI) system for predicting hemodynamic parameters for a target vessel, the AI system comprising:
a first interface configured to receive a vessel shape model of the target vessel;
a second interface configured to receive a flow profile of the target vessel; and
an AI unit communicatively connected to the first interface and communicatively connected to the second interface, the AI unit configured to iteratively predict at least one hemodynamic parameter based on the vessel shape model and the flow profile, wherein
the iterative prediction of the at least one hemodynamic parameter includes predicting the at least one hemodynamic parameter for a first vessel shape point based on the first vessel shape point and the flow profile and for a second vessel shape point based on the second vessel shape point and a hidden state of the first vessel shape point,
the first vessel shape point and the second vessel shape point are consecutive vessel shape points of the vessel shape model, and
the flow profile is an inlet flow profile for the target vessel at the first vessel shape point.

9. The AI system of claim 8, wherein the AI unit comprises a Recurrent Neural Network (RNN).

10. The AI system of claim 8, wherein the AI unit comprises:
a first input block communicatively connected to the first interface, the first input block configured to receive the first vessel shape point at a first iteration and the second vessel shape point at a second iteration;
a second input block communicatively connected to the second interface, the second input block configured to receive the flow profile at a first iteration;
a deduction block communicatively connected to the first input block and communicatively connected to the second input block, the deduction block configured to generate at least one first current hidden state based on the first vessel shape point and on the flow profile, and generate at least one second current hidden state based on the second vessel shape point and the at least one first current hidden state; and an output block communicatively connected to the deduction block, the output block configured to
determine the at least one hemodynamic parameter based at least on a last generated current hidden state of the at least one first current hidden state for the first vessel shape point, and
determine the at least one hemodynamic parameter based at least on a last generated current hidden state of the at least one second current hidden state.

11. The AI system of claim 10, wherein the AI unit further comprises:
a first deduction layer communicatively connected to the first input block and communicatively connected to the second input block, the first deduction layer configured to
generate a current hidden state of the at least one first current hidden state based on the first vessel shape point and the flow profile, and
generate a current hidden state of the at least one second current hidden state based on the second vessel shape point and the current hidden state of the of the at least one first current hidden state;
at least one further deduction layer communicatively connected to the first deduction layer, the at least one further deduction layer configured to
generate at least one further current hidden state of the at least one first current hidden state based on a current hidden state of a previous deduction layer of a first iteration, and
generate at least one further current hidden state of the at least one second current hidden state based on a current hidden state of a previous deduction layer of a second iteration and the at least one first current hidden state of the at least one first current hidden state; and
a last deduction layer communicatively connected to a last of the at least one further deduction layer, the last deduction layer configured to
generate a last current hidden state of the at least one first current hidden state based on a current hidden state of a last of the at least one further deduction layer of the first iteration, and
generate a last current hidden state of the at least one second current hidden state based on a current hidden state of a last of the at least one further deduction layer of the second iteration and the last current hidden state of the at least one first current hidden state.

12. The AI system of claim 11, wherein the first input block is configured to receive one of the consecutive vessel shape points including one consecutive centerline point on a centerline along a main direction of the target vessel and a number of surrounding points surrounding each centerline point in a form of a sphere with each respective centerline point in the center of each respective sphere at each respective iteration,
wherein the first deduction layer is configured to
generate the current hidden state of the at least one first current hidden state based on the first vessel shape point including the respective centerline point and the number of surrounding points surrounding the centerline point and on the flow profile, and
generate a current hidden state of the at least one second current hidden state based on the second vessel shape point and the current hidden state of the at least one first current hidden state, wherein the at least one further deduction layer is configured to
generate at least one set of further current hidden states of the at least one first current hidden state based on a current hidden state of a previous deduction layer of the first iteration, and
generate at least one set of further current hidden states of the at least one second current hidden state based on a current hidden state of a previous deduction layer of the second iteration and a current further hidden state of the at least one set of further current hidden states of the at least one first current hidden state, wherein the last deduction layer is configured to
generate a last current hidden state of the at least one first current hidden state based on a current hidden state of a last of the at least one further deduction layer of the first iteration, and
generate a last current hidden state of the at least one second current hidden state based on a current hidden state of a last of the at least one further deduction layer of the second iteration and the last current hidden state of the at least one first current hidden state, and wherein the output block is configured to
determine the at least one hemodynamic parameter of the first vessel shape point based at least on the last current hidden state of the at least one first current hidden state, and
determine the at least one hemodynamic parameter of the second vessel shape point based at least on the last current hidden state of the at least one second current hidden state.

13. The AI system of claim 10, wherein the output block comprises:
at least one concatenation layer communicatively connected to the deduction block; and
an output layer communicatively connected to a last of the at least one concatenation layer and communicatively connected to the deduction block,
wherein the at least one concatenation layer and the output layer are jointly configured to determine the at least one hemodynamic parameter of the first vessel shape point based at least on the at least one first current hidden state and to determine the at least one hemodynamic parameter of the second vessel shape point based at least on the at least one second current hidden state.

14. A non-transitory computer-readable medium storing a program which, when executed by a computer, causes the computer to carry out the method of claim 1.

15. A computer-implemented method of training an Artificial Intelligence (AI) unit, the computer-implemented method comprising:
receiving an input training dataset including training vessel shape models and corresponding training flow profiles, the corresponding training flow profiles being acquired by a medical imaging system;
receiving an output training dataset corresponding to the training input dataset including at least one training hemodynamic parameters; and
training the AI unit to predict at least one hemodynamic parameter of a target vessel with the training vessel shape models and corresponding training flow profiles and the output training dataset, wherein each training flow profile is an inlet flow profile for a vessel at a first vessel shape point of a corresponding vessel shape model.

16. The computer-implemented method of claim 15, further comprising:
determining a shape variability and a geometric variability of a vessel within a given population by applying a statistical shape analysis on a set of real vessel shape models of the vessel;
synthesizing at least one synthetic vessel shape model of the vessel based on the shape variability and geometric variability of the vessel within the given population;
determining corresponding training flow profiles for at least one of the at least one synthetic vessel shape model or the set of real vessel shape models;
aggregating the input training dataset with the set of real shape models, the at least one synthetic vessel shape model and the corresponding training flow profiles; and
computing corresponding at least one training hemodynamic parameters of the output training dataset based on at least one of the set of real vessel shape models or the at least one synthetic vessel shape model, and based on the corresponding training flow profiles of the input training dataset.

17. The computer-implemented method of claim 15, wherein the training hemodynamic parameters of the output training dataset are computed using Computational Fluid Dynamic (CFD) simulations.

18. A non-transitory computer-readable medium storing a program which, when executed by a computer, causes the computer to carry out the computer-implemented method of claim 15.

19. The method of claim 1, wherein the vessel shape model includes a dataset representing a polygonal mesh or volumetric meshes formed from vertices, tetrahedra, hexahedra, or other 3D elements and the flow profile includes features of blood flow in the target vessel.

20. The method of claim 1, wherein the hidden state of the first vessel shape point is a first current hidden state generated by a deduction block of the AI unit.

21. The method of claim 1, wherein the first vessel shape point, the flow profile, and the second vessel shape point are input into one or more input blocks of the AI unit and the at least one hemodynamic parameter is output at an output block of the AI unit.

* * * * *